United States Patent
Kim et al.

(10) Patent No.: US 7,973,306 B2
(45) Date of Patent: Jul. 5, 2011

(54) ANTHRACENE DERIVATIVES, ORGANIC ELECTRONIC DEVICES USING ANTHRACENE DERIVATIVES, AND ELECTRONIC APPARATUSES COMPRISING ORGANIC ELECTRONIC DEVICE

(75) Inventors: Ji-Eun Kim, Daejeon (KR); Jae-Chol Lee, Daejeon (KR); Hye-Young Jang, Daejeon (KR); Tae-Yoon Park, Daejeon (KR); Sung-Kil Hong, Daejeon (KR); Jun-Gi Jang, Daejeon (KR); Jin-Kyoon Park, Daejeon (KR); Hyun Nam, Seoul (KR); Kong-Kyeom Kim, Daejeon (KR); Yeon-Hwan Kim, Goyang-si (KR)

(73) Assignee: LG Chem, Ltd., Seoul (KR)

( * ) Notice: Subject to any disclaimer, the term of this patent is extended or adjusted under 35 U.S.C. 154(b) by 259 days.

(21) Appl. No.: 12/309,612

(22) PCT Filed: Jul. 25, 2007

(86) PCT No.: PCT/KR2007/003566
§ 371 (c)(1),
(2), (4) Date: Jan. 23, 2009

(87) PCT Pub. No.: WO2008/013399
PCT Pub. Date: Jan. 31, 2008

(65) Prior Publication Data
US 2010/0001262 A1    Jan. 7, 2010

(30) Foreign Application Priority Data

Jul. 26, 2006  (KR) .................. 10-2006-0070354

(51) Int. Cl.
*H01L 51/54* (2006.01)
*C07C 13/32* (2006.01)

(52) U.S. Cl. ............... 257/40; 257/E51.049; 585/26
(58) Field of Classification Search ............ 257/40, 257/E51.001–E51.052; 313/504; 428/690, 428/917; 438/99
See application file for complete search history.

(56) References Cited

U.S. PATENT DOCUMENTS

| 2005/0064233 | A1  | 3/2005  | Matsuura et al. |
| 2005/0211958 | A1  | 9/2005  | Conley et al. |
| 2005/0271899 | A1  | 12/2005 | Brown et al. |
| 2006/0019116 | A1  | 1/2006  | Conley et al. |
| 2007/0106103 | A1* | 5/2007  | Ikeda et al. ............ 585/26 |
| 2007/0207342 | A1* | 9/2007  | Royster et al. ........ 428/690 |
| 2007/0252521 | A1* | 11/2007 | Kondakov et al. ...... 313/506 |
| 2008/0093986 | A1  | 4/2008  | Inoue et al. |
| 2008/0111473 | A1* | 5/2008  | Kawamura et al. ..... 313/504 |

FOREIGN PATENT DOCUMENTS

TW        200406133        4/2004
(Continued)

*Primary Examiner* — Matthew W Such
(74) *Attorney, Agent, or Firm* — McKenna Long & Aldridge LLP

(57) ABSTRACT

Disclosed in an anthracene derivative, an organic electronic device using the anthracene derivative, and an electronic apparatus including the organic electronic device. The anthracene derivative is capable of being used as a hole injecting material, a hole transporting material, an electron injecting material, an electron transporting material, and a light emitting material in an organic electronic device including an organic light emitting device. In particular, the anthracene derivative is capable of being used alone as a light emitting material and a host or a dopant in a host/dopant system. The organic electronic device is excellent in views of efficiency, driving voltage, life time, and stability.

14 Claims, 4 Drawing Sheets

FOREIGN PATENT DOCUMENTS

| | | |
|---|---|---|
| TW | 200803616 | 1/2008 |
| WO | WO 2005056505 A1 * | 6/2005 |
| WO | WO 2006067931 A1 * | 6/2006 |
| WO | WO 2006/070711 A1 | 7/2006 |
| WO | WO 2007/102683 A1 | 9/2007 |
| WO | WO 2007105884 A1 * | 9/2007 |

* cited by examiner

[Fig. 1]
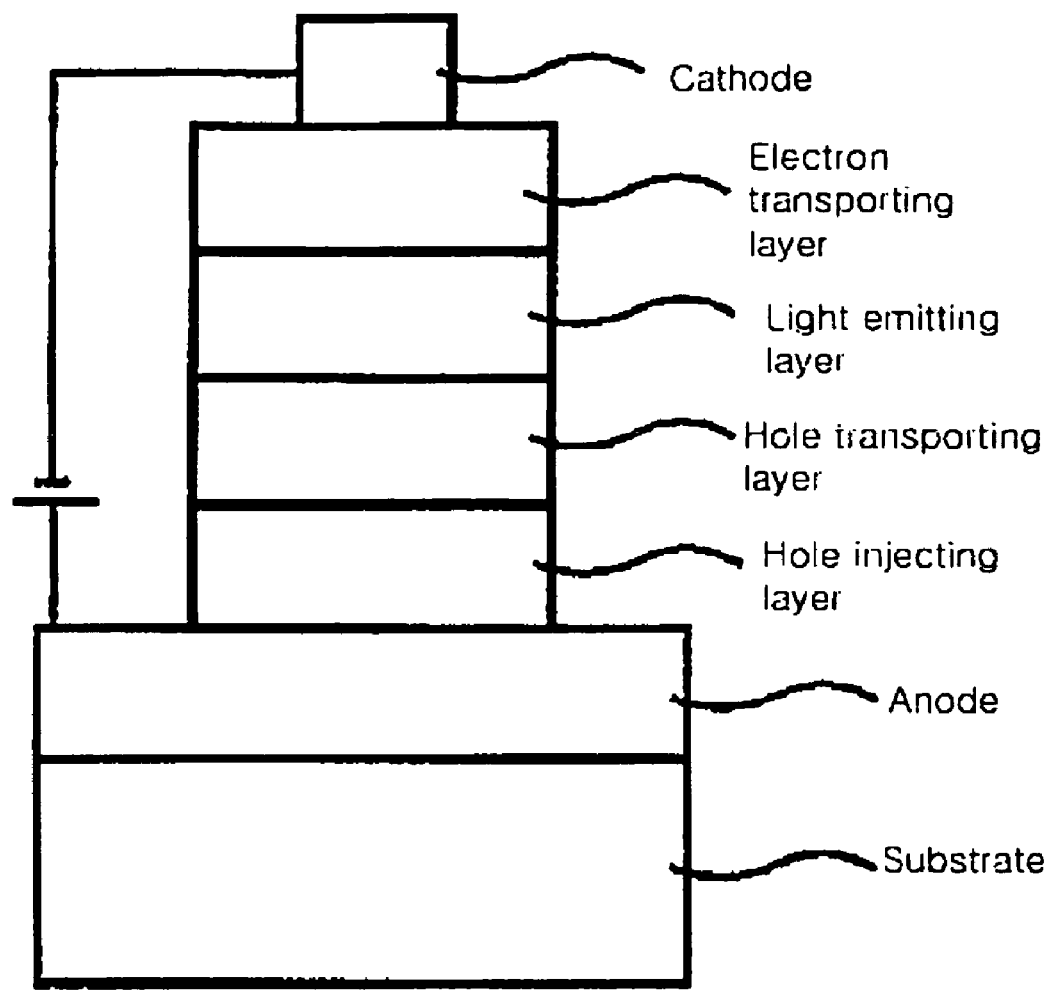

[Fig. 2]
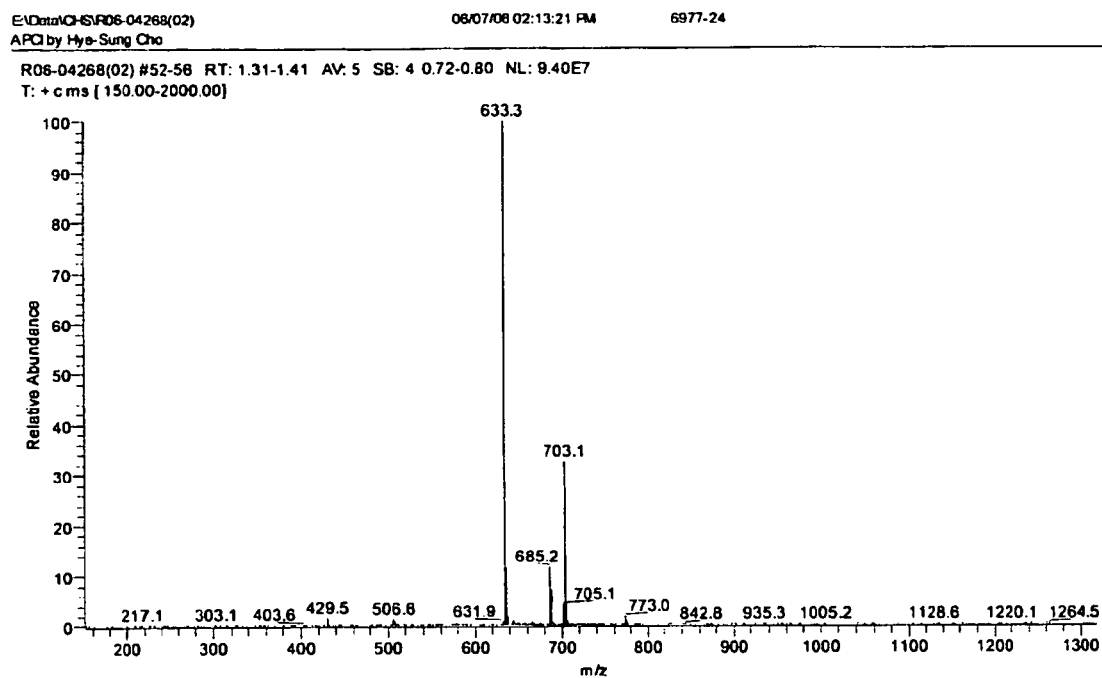

[Fig. 3]
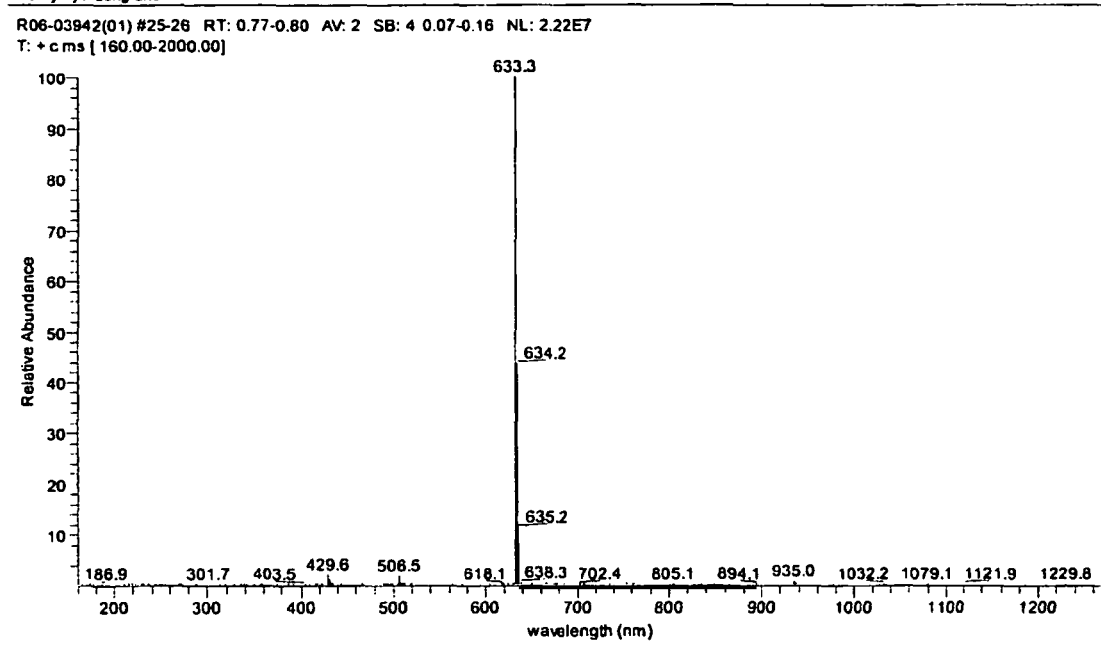

[Fig. 4]
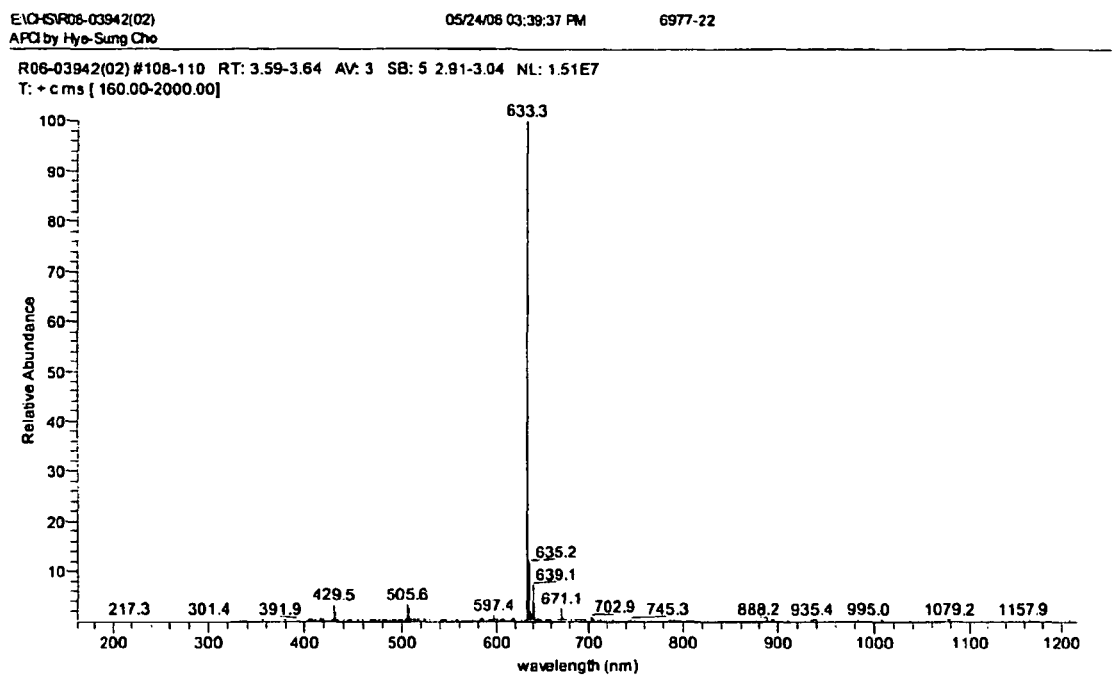

ANTHRACENE DERIVATIVES, ORGANIC ELECTRONIC DEVICES USING ANTHRACENE DERIVATIVES, AND ELECTRONIC APPARATUSES COMPRISING ORGANIC ELECTRONIC DEVICE

This application claims priority to PCT/KR2007/003566 filed on Jul. 25, 2007 and also Korean Patent Application No. 10-2006-0070354 filed on Jul. 26, 2006, the contents of which are hereby incorporated by reference in their entirety.

TECHNICAL FIELD

The present invention relates to an anthracene derivative, an organic electronic device using the anthracene derivative, and an electronic apparatus comprising the organic electronic device.

This application claims priority from Korea Patent Application No. 10-2006-0070354 filed on Jul. 26, 2006 in the KIPO, the disclosure of which is incorporated herein by reference in its entirety.

BACKGROUND ART

The term "organic electronic device" refers to a device requiring charge exchange between an electrode and an organic material by using holes and electrons. The organic electronic device may be largely classified into two types according to the operational mechanism. One type is an electronic device in which an exciton is formed in an organic material layer by photons provided from an external light source to the device, the exciton is divided into an electron and a hole, the electron and the hole are transported to respective electrodes to be used as a current source (voltage source). The other type is an electronic device in which a hole and/or an electron is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC), and an organic transistor. The above-mentioned examples of the organic electronic device all require a hole injecting or transporting material, an electron injecting or transporting material, or a light emitting material in order to drive the device.

Hereinafter, the organic light emitting device will be described in detail. The hole injecting or transporting material, the electron injecting or transporting material, and the light emitting material of the above-mentioned organic electronic devices act like those of the organic light emitting device as described later.

Generally, organic light emission means that electric energy is converted into light energy by using an organic material. An organic light emitting device using the organic light emission phenomenon typically includes an anode, a cathode, and an organic material layer that is interposed between the anode and the cathode. The organic material layer is to have a multilayered structure made of different materials in order to improve efficiency and stability of the organic light emitting device. For example, the organic material layer may be formed of a hole injection layer, a hole transporting layer, a light emitting layer, an electron transporting layer, and an electron injection layer. If voltage is applied between two electrodes in the organic light emitting device having the above-mentioned structure, a hole is injected into the organic material layer at an anode and an electron is injected into the organic material layer at a cathode. When the hole meets the electron, an exciton is generated, and light is generated when the exciton is converted into a bottom state. It is known that the organic light emitting device has properties such as self-light emission, high luminance, high efficiency, low driving voltage, wide viewing angle, high contrast, and high-speed response.

The materials used for the organic material layer of the organic light emitting device may be classified into a light emitting material and a charge transporting material, for example, a hole injecting material, a hole transporting material, an electron transporting material, and an electron injecting material according to the type of function. Further, the light emitting material may be classified into a high molecular weight type and a low molecular weight type according to a molecular weight and into a fluorescent material on the basis of a singlet excitation state of electrons and a phosphorescence material on the basis of a triplet excitation state of electrons according to the type of light emitting mechanism. Additionally, the light emitting material may be classified into a blue, green, or red light emitting material and a yellow or orange light emitting material required to ensure a better natural color according to a light emitting color.

Meanwhile, an efficiency of a device is lowered owing to maximum luminescence wavelength moved to a longer wavelength due to the interaction between molecules, deterioration of color purity, and reduction in light emitting efficiency when only one material is used as the light emitting material, and therefore, a host/dopant system may be used as the light emitting material for the purpose of enhancing color purity and light emitting efficiency through energy transfer. This is based on a mechanism where if a dopant having an energy band interval lower than that of a host constituting the light emitting layer is mixed with the light emitting layer in a small amount, an exciton that is generated from the light emitting layer is transported to the dopant to emit light at high efficiency. In this connection, since the wavelength of the host is moved toward the wavelength of the dopant, it is possible to obtain light having a desired wavelength according to the type of dopant.

In order to allow the organic light emitting device to fully exhibit the above-mentioned excellent characteristics, a material constituting the organic material layer in the device, for example, a hole injecting material, a hole transporting material, a light emitting material, an electron transporting material, and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required in the above-mentioned other organic electronic devices.

DISCLOSURE OF INVENTION

Technical Problem

Therefore, the present inventors have synthesized a novel anthracene derivative and found that the anthracene derivative is capable of being used as a hole injecting material, a hole transporting material, an electron injecting material, an electron transporting material, and a light emitting material in an organic electronic device. Furthermore, they have found that the derivative is capable of being used alone as a light emitting material and a host or a dopant in a host/dopant system, and the organic electronic device containing the anthracene derivative has increased efficiency, reduced driving voltage, and the improved life and stability. Accordingly, it is an object of the present invention to provide an anthracene derivative, an organic electronic device using the anthracene derivative, and an electronic apparatus including the organic electronic device.

Technical Solution

The present invention provides an anthracene derivative represented by the Formula 1:

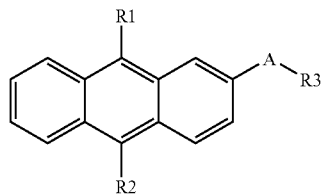

[Formula 1]

wherein R1, R2, and R3 are each independently a $C_6$ to $C_{20}$ aryl group, and
A is

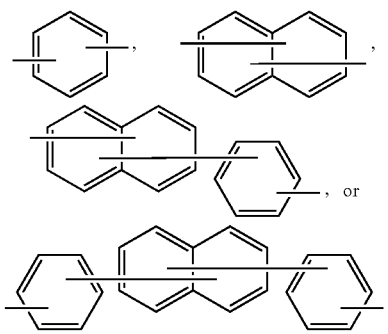

with a proviso that R3 is not phenyl when A is phenylene.

Furthermore, the present invention provides an organic electronic device using the anthracene derivative.

Furthermore, the present invention provides an electronic apparatus that includes the organic electronic device.

Advantageous Effects

An anthracene derivative according to the present invention is capable of being used as a hole injecting material, a hole transporting material, an electron injecting material, an electron transporting material, and a light emitting material in an organic electronic device including an organic light emitting device. In particular, the derivative is capable of being used alone as a light emitting material and a host or dopant in a host/dopant system. The organic electronic device according to the present invention is excellent in views of efficiency, driving voltage, life time, and stability.

BRIEF DESCRIPTION OF THE DRAWINGS

FIG. 1 is a view illustrating a structure of an organic light emitting device according to an embodiment of the present invention;

FIG. 2 is a MS graph of an anthracene derivative represented by Formula 1-1 according to the present invention;

FIG. 3 is a MS graph of an anthracene derivative represented by Formula 1-2 according to the present invention; and FIG. 4 is a MS graph of an anthracene derivative represented by Formula 1-5 according to the present invention.

BEST MODE FOR CARRYING OUT THE INVENTION

A detailed description of the present invention will be given hereinafter.

The present invention provides an anthracene derivative represented by the Formula 1.

Substituent groups that are shown in the Formula 1 will be described in detail.

R1, R2 and R3 are each independently a $C_6$ to $C_{20}$ aryl group, and preferably any one selected from phenyl, naphthyl, and biphenyl.

It is preferable that A be any one group selected from the following substituent groups.

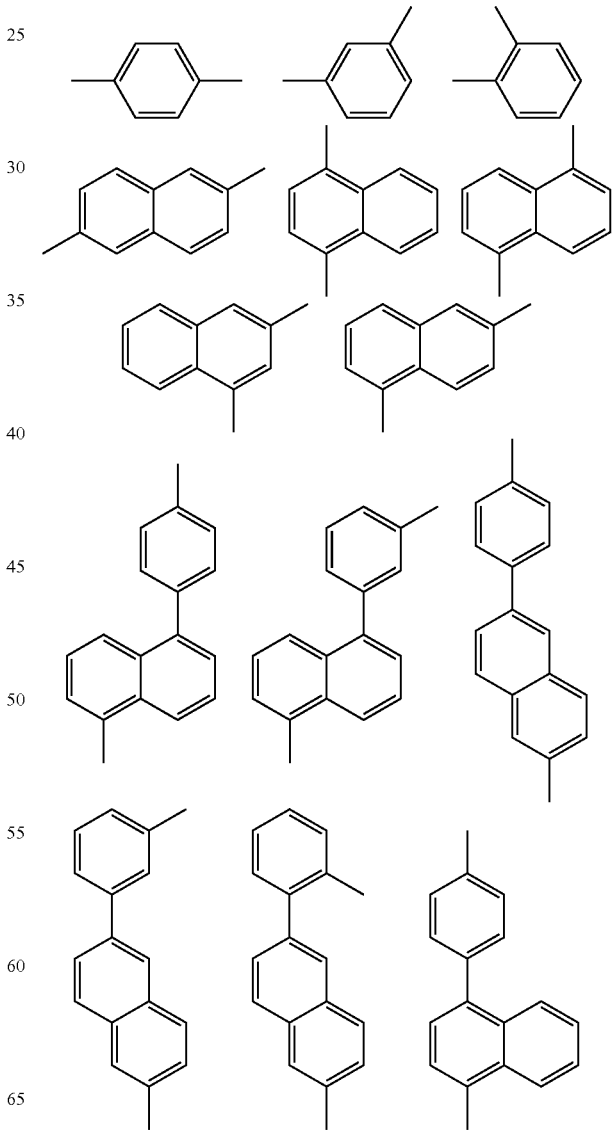

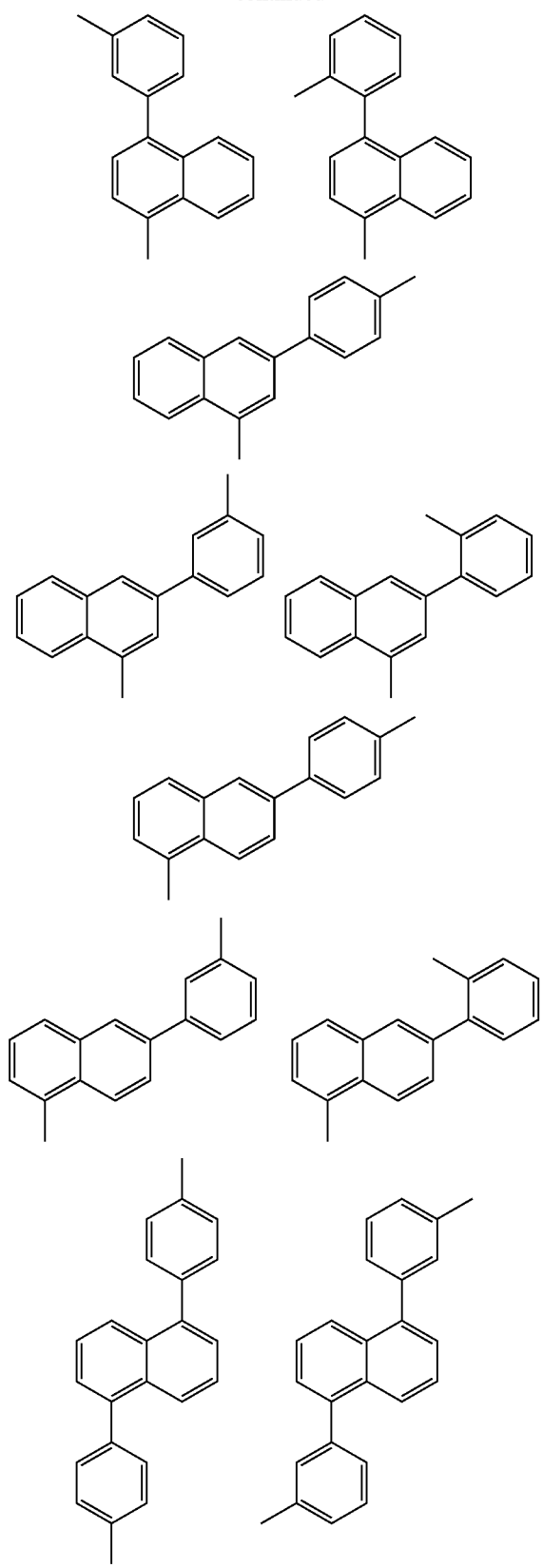
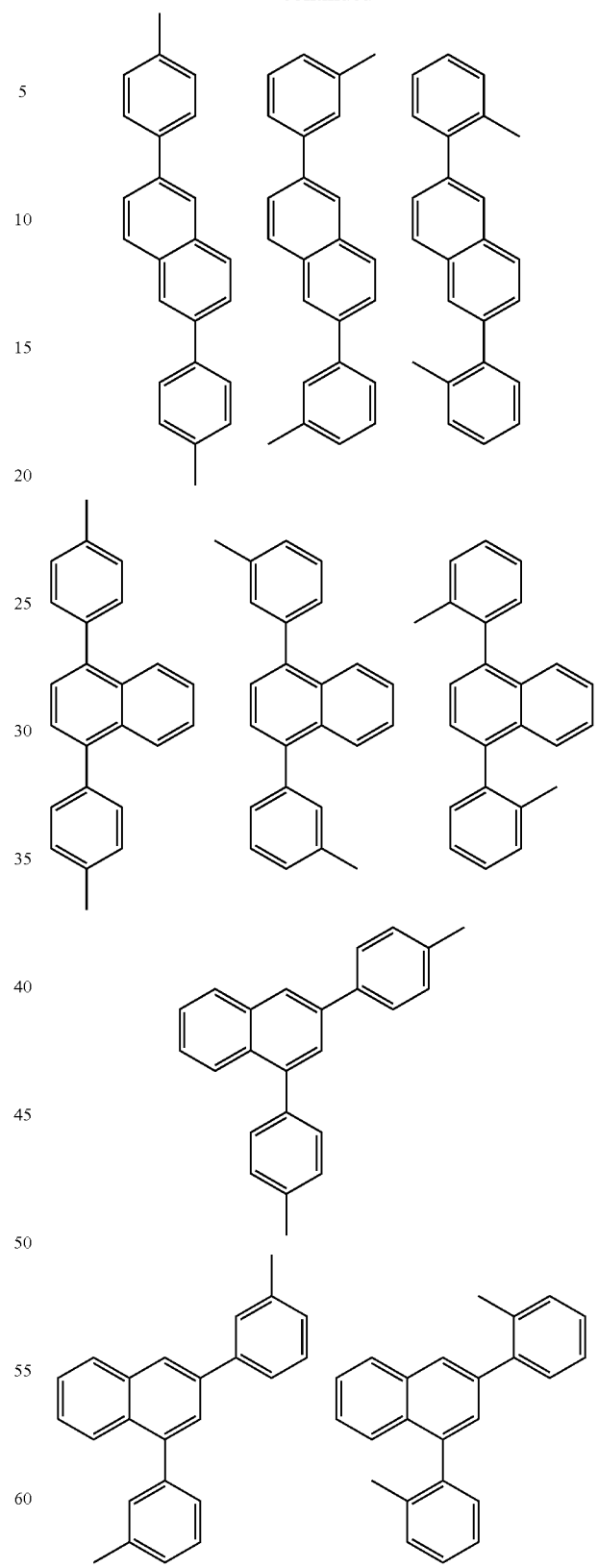

-continued
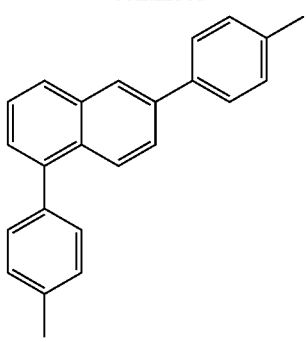
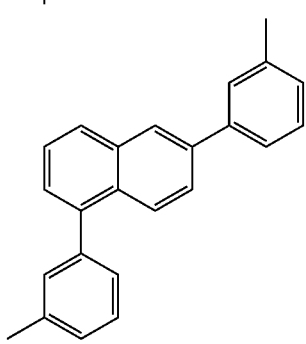
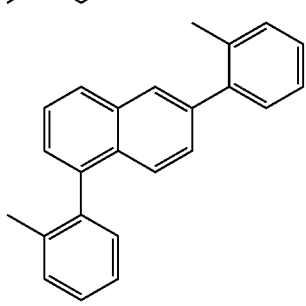
Specific examples of the anthracene derivative that is represented by Formula 1 according to the present invention include, but are not limited to compounds represented by the Formulae 1-1 to 1-27.
<Formula 1-1>
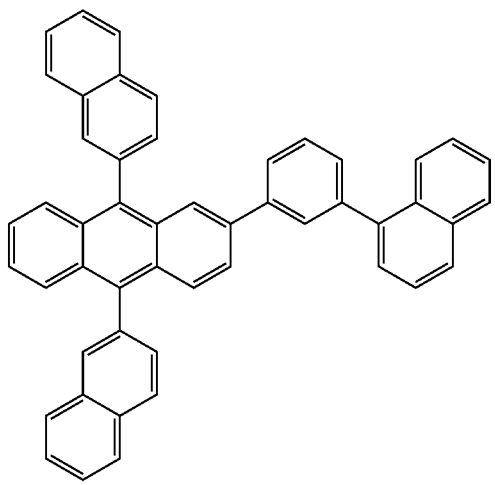
<Formula 1-2>
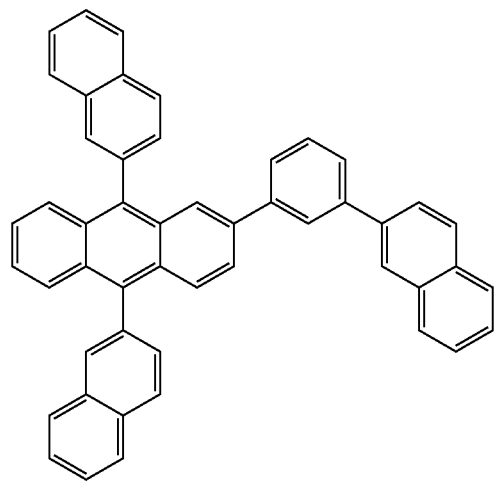
<Formula 1-3>
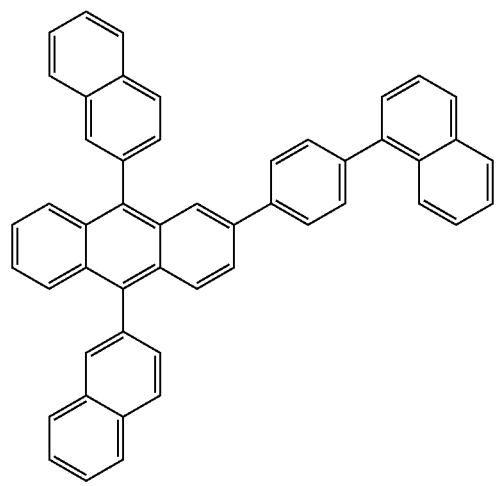
<Formula 1-4>
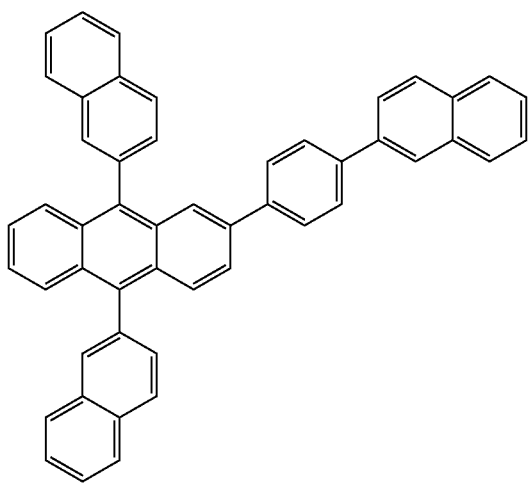

<Formula 1-5>
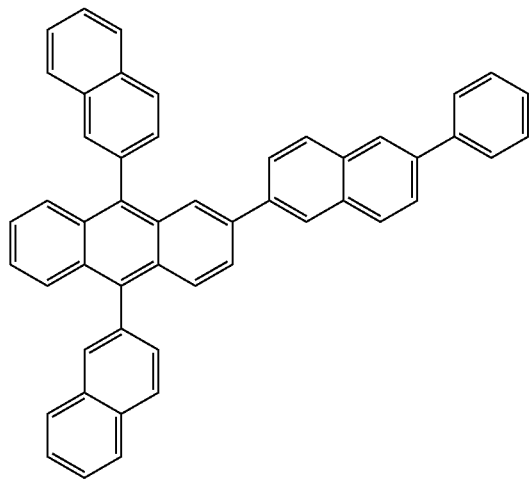
<Formula 1-6>
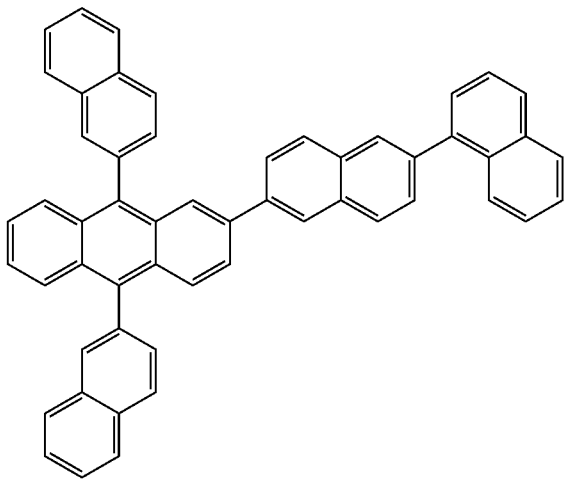
<Formula 1-7>
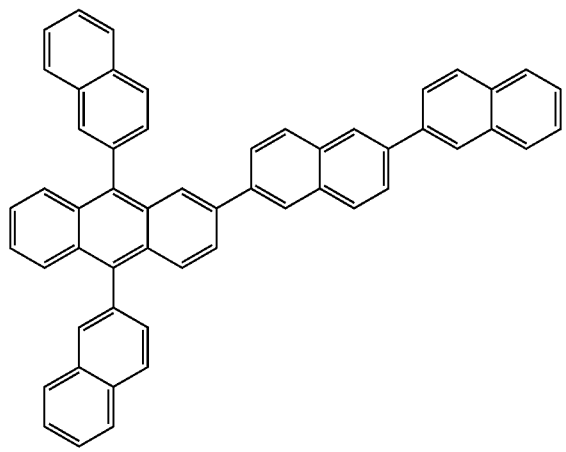
<Formula 1-8>
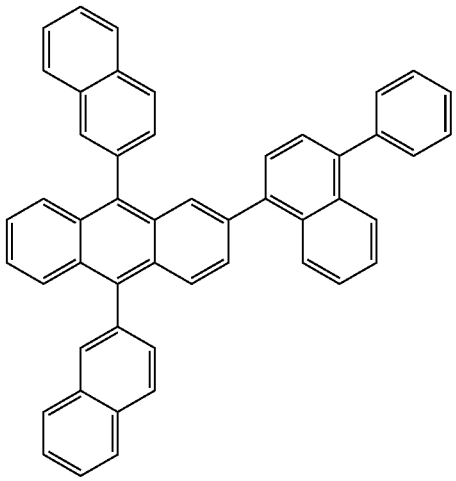
<Formula 1-9>
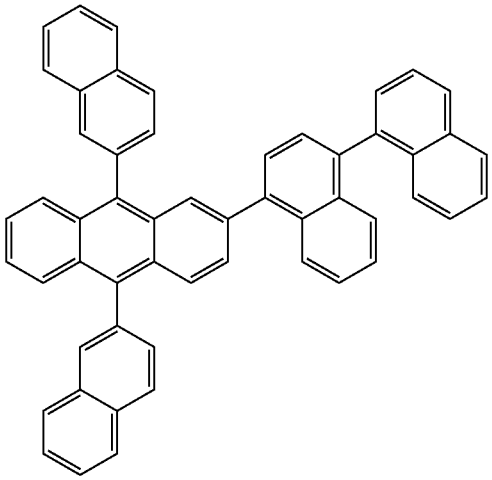
<Formula 1-10>
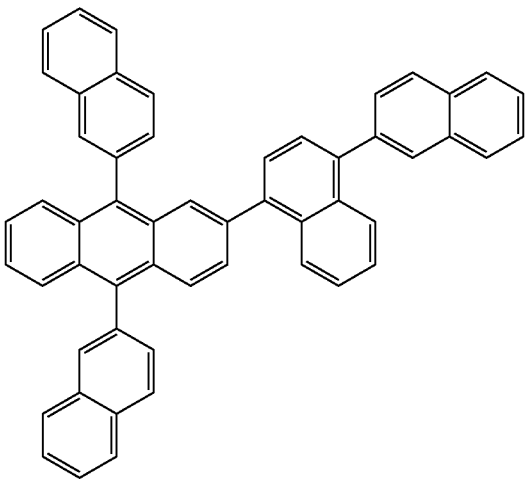

<Formula 1-11>
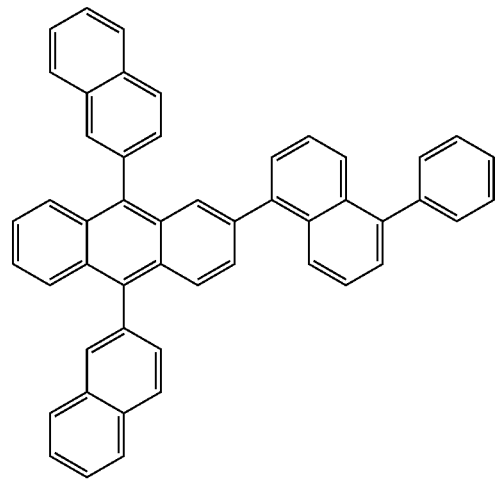
<Formula 1-14>
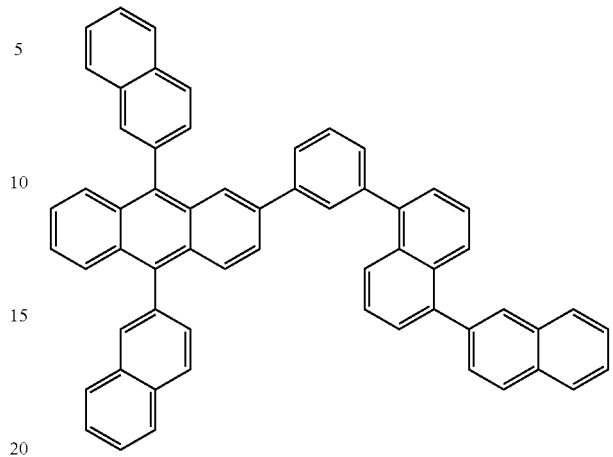
<Formula 1-12>
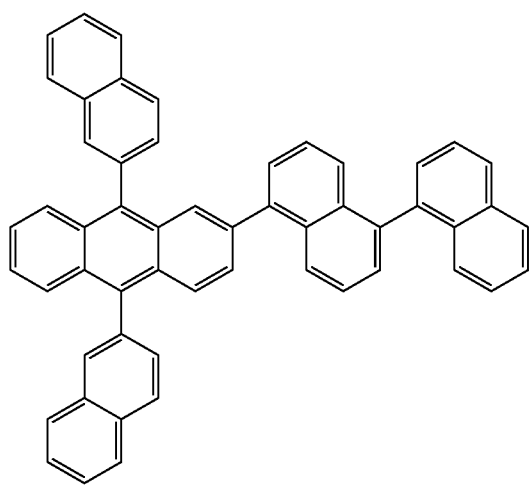
<Formula 1-15>
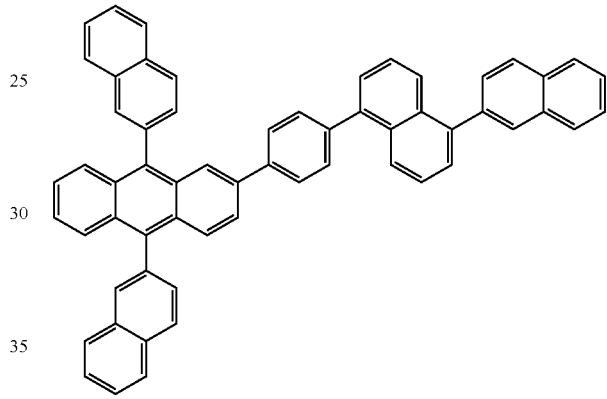
<Formula 1-13>
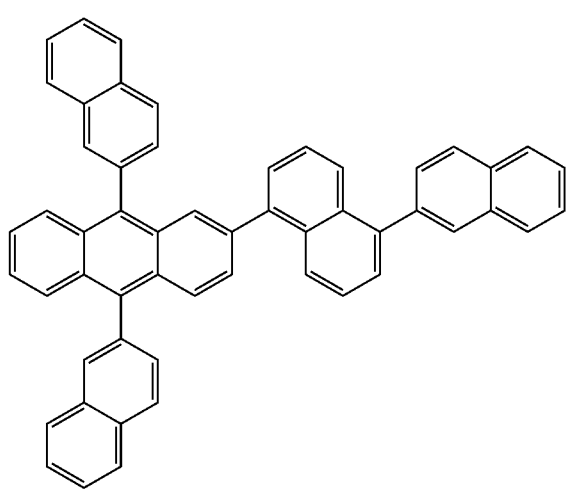
<Formula 1-16>
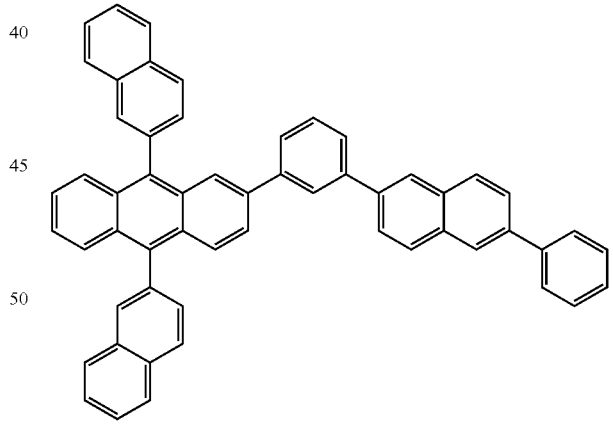

<Formula 1-17>
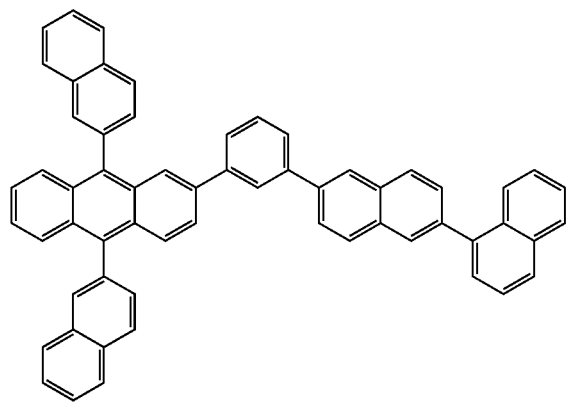
<Formula 1-18>
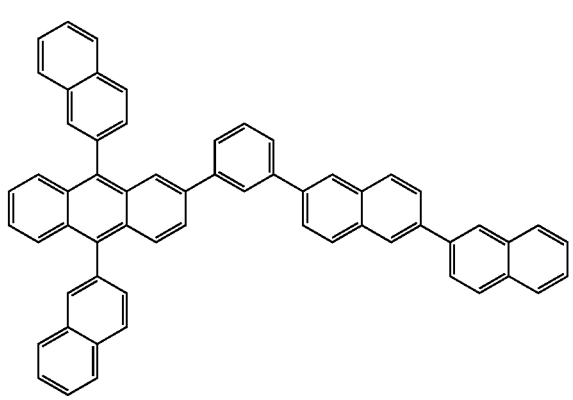
<Formula 1-19>
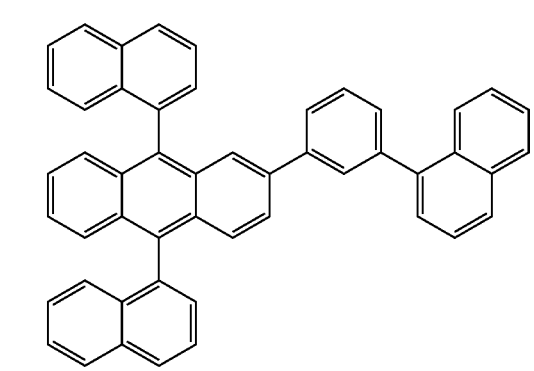
<Formula 1-20>
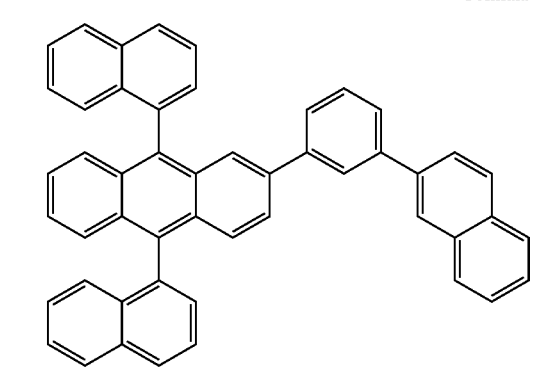
<Formula 1-21>
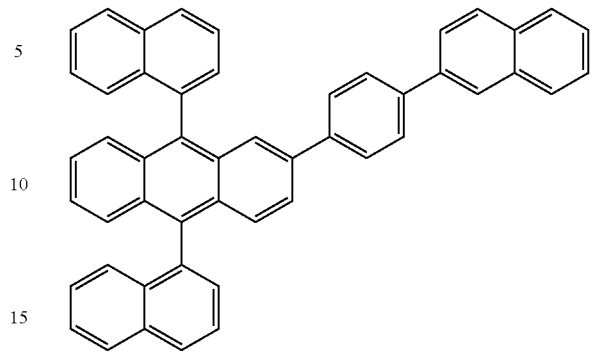
<Formula 1-22>
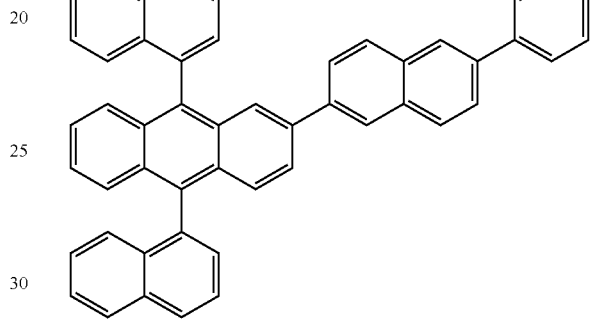
<Formula 1-23>
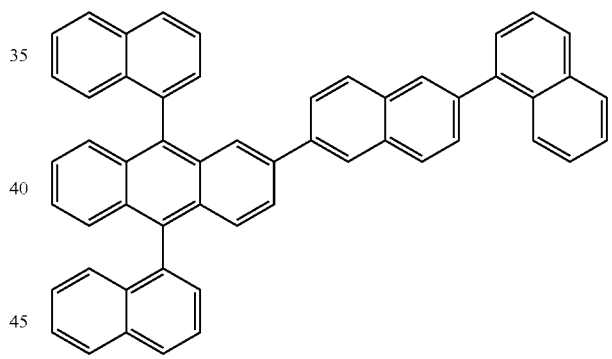
<Formula 1-24>
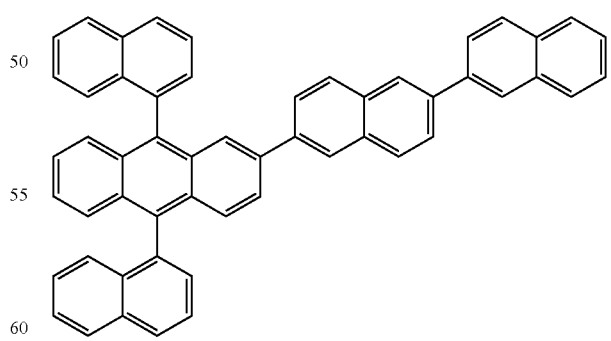

<Formula 1-25>

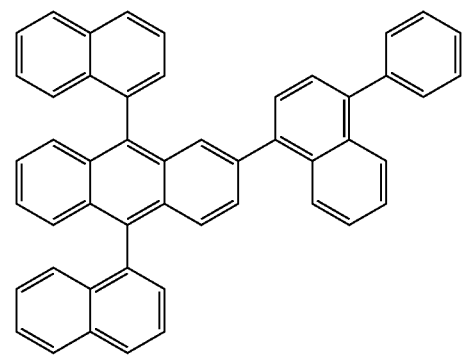

<Formula 1-26>

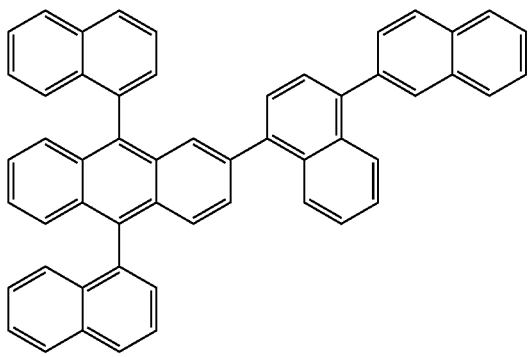

<Formula 1-27>

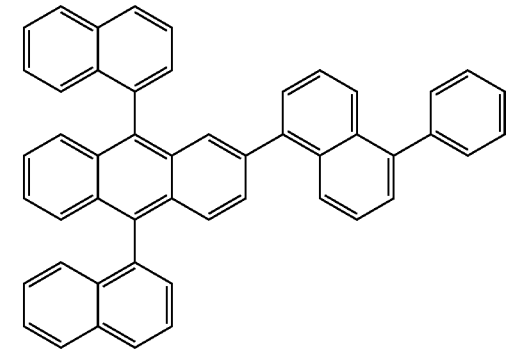

The anthracene derivative that is represented by Formula 1 according to the present invention may be produced by using the following typical production process.

A halide aryl compound and an anthracene boronic acid compound which is substituted with aryl groups at 9 and 10 positions thereof may be subjected to a Suzuki coupling reaction in the presence of a palladium catalyst to produce the anthracene derivative.

The specific production process will be described in Synthetic Examples as described later.

The present invention provides an organic electronic device that uses the anthracene derivative represented by Formula 1. Examples of the organic electronic device include an organic light emitting device, an organic solar cell, an organic photoconductor, an organic transistor, an organic laser, an electromagnetic wave blocking film, a capacitor, and a memory device.

The organic electronic device according to the present invention may be produced by means of a typical material using a typical process of producing an organic electronic device, except that one or more organic material layers are formed by using the anthracene derivative.

Hereinafter, the organic light emitting device, which is an example of the organic electronic device, will be described in detail.

The above-mentioned anthracene derivative according to the present invention may act as a hole injecting, hole transporting, electron injecting, electron transporting, or light emitting material in the organic light emitting device. In particular, the above-mentioned anthracene derivative may act as a light emitting host in conjunction with an appropriate light emitting dopant and may be used alone as a light emitting material, a host, or a dopant.

In an embodiment of the present invention, the organic light emitting device may include a first electrode, a second electrode, and an organic material layer that is interposed between the electrodes. The organic light emitting device may be produced by means of a typical material using a typical process of producing an organic light emitting device, except that one or more organic material layers are formed in the organic light emitting device by using the anthracene derivative according to the present invention. The structure of the organic light emitting device according to the present invention is shown in FIG. 1, but the scope of the present invention is not limited thereto.

For example, the process of producing the organic light emitting device according to the present invention includes depositing metal, metal oxides having conductivity, or an alloy thereof on a substrate by using a PVD (physical vapor deposition) method such as sputtering or e-beam evaporation to form an anode, forming an organic material layer that includes a hole injecting layer, a hole transporting layer, a light emitting layer, an electron transporting layer, or the like thereon, and depositing a material that is capable of being used to form a cathode thereon. In addition to the above-mentioned method, another method may be used. For example, the cathode material, the organic material layer, and the anode material may be sequentially deposited on the substrate to produce the organic light emitting device.

The organic material layer may have a multilayered structure that includes the hole injecting layer, the hole transporting layer, the light emitting layer, the electron transporting layer, and the like. However, the structure of the organic material layer is not limited thereto, and the organic material layer may have a single layer structure. In addition, the organic material layer may be produced by means of various types of polymer materials by using not a deposition method but a solvent process such as spin coating, dip coating, doctor blading, screen printing, inkjet printing, heat transfer method or the like so that the organic material layer has a small number of layers.

It is preferable that the anode material have a large work function so that a hole is desirably injected into the organic material layer. Specific examples of the anode material include, but are not limited to metal such as vanadium, chrome, copper, zinc, and gold, or an alloy thereof; metal oxides such as zinc oxides, indium oxides, indium tin oxides (ITO), and indium zinc oxides (IZO); metal/oxide composites such as $ZnO:Al$ or $SnO_2:Sb$; and conductive polymers such as poly(3-methylthiophene), poly[3,4-(ethylene-1,2-dioxy) thiophene] (PEDT), polypyrrole, and polyaniline.

It is preferable that the cathode material have a small work function so that an electron is desirably injected into the organic material layer. Specific examples of the cathode material include, but are not limited to metal such as magnesium, calcium, sodium, potassium, titanium, indium, yttrium, lithium, gadolinium, aluminum, silver, tin, and lead, or an alloy thereof: and a multilayered material such as LiF/Al or LiO$_2$/Al.

The hole injecting material is a material that is capable of desirably receiving a hole from an anode at low voltage. It is preferable that the HOMO (highest occupied molecular orbital) level of the hole injecting material be located between the work function of the anode material and the HOMO level of its neighboring organic material layer. Specific examples of the hole injecting material include, but are not limited to organic materials of metal porphyrin, oligothiophene, and arylamine series, organic materials of hexanitrile hexaazatriphenylene and quinacridone series, organic materials of perylene series, and conductive polymers of on anthraquinone, polyaniline, and polythiophene series.

The hole transporting material is suitably a material having high hole mobility, which is capable of transferring holes from the anode or the hole injecting layer toward the light emitting layer. Specific examples of the hole transporting material include, but are not limited to organic materials of arylamine series, conductive polymers, and block copolymers having both conjugated portions and non-conjugated portions.

The light emitting material is a material capable of emitting visible light by accepting and recombining holes from the hole transporting layer and electrons from the electron transporting layer, and preferably a material having high quantum efficiency for fluorescence and phosphorescence. Specific examples of the light emitting material include, but are not limited to 8-hydroxyquinoline aluminum complex (Alq$_3$); compounds of carbazole series; dimerized styryl compounds; BAlq; 10-hydroxybenzoquinoline-metal compounds; compounds of benzoxazole, benzthiazole, and benzimidazole series; polymers of poly(p-phenylenevinylene) (PPV) series; spiro compounds; and compounds of polyfluorene and rubrene series.

The electron transporting material is suitably a material having high electron mobility, which is capable of transferring electrons from the cathode to the light emitting layer. Specific examples of the electron transporting material include, but are not limited to 8-hydroxyquinoline aluminum complex (Alq$_3$); complexes including Alq$_3$; organic radical compounds; and hydroxyflavone-metal complexes.

The organic light emitting device according to the present invention may be a top light emitting type, a bottom light emitting type, or a dual-sided light emitting type according to the type of material used.

The anthracene derivative according to the present invention may act according to a principle similar to that applied to the organic light emitting device in an organic electronic device including an organic solar cell, an organic photoconductor, and an organic transistor.

The present invention provides an electronic apparatus that comprises the organic electronic device. Examples of the electronic apparatus include display apparatuses, smart cards, sensors, and electronic tags (RFID; Radio Frequency Identification).

The electronic apparatus may be produced by using a typical production method known in the related art, except that the electronic apparatus comprises the organic electronic device according to the present invention.

Mode For The Invention

Hereinafter, the present invention will be described in detail in light of Synthetic Examples and Experimental Examples. The present invention may, however, be embodied in many different forms and should not be construed as being limited to the Synthetic Examples and Experimental Examples set forth herein. Rather, these Synthetic Examples and Experimental Examples are provided such that this disclosure will be thorough and complete and will fully convey the concept of the present invention to those skilled in the art.

The anthracene derivative according to the present invention may be produced by a multi-stage chemical reaction described in Synthetic Examples 1 to 7. As described in Synthetic Examples, intermediate compounds are first produced, and the anthracene derivative is produced from the intermediate compounds.

SYNTHETIC EXAMPLE 1

Production of Compound of Formula 1-1

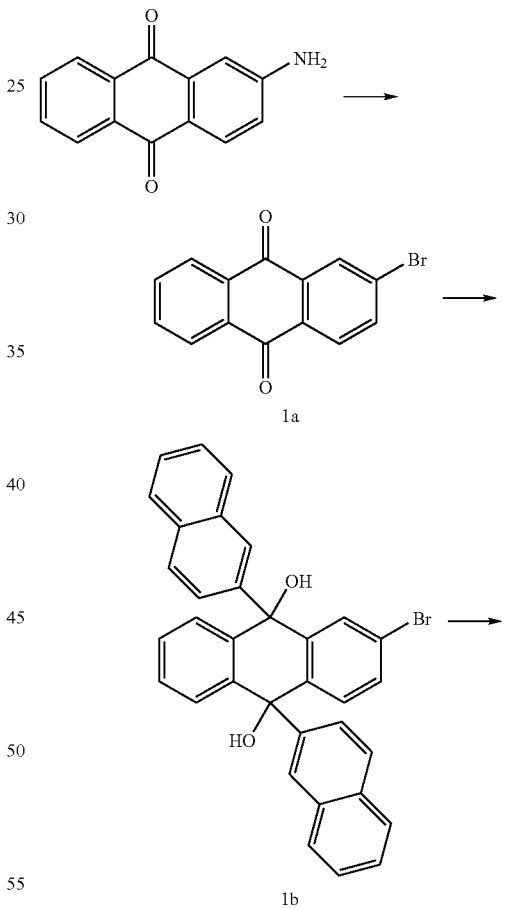

-continued

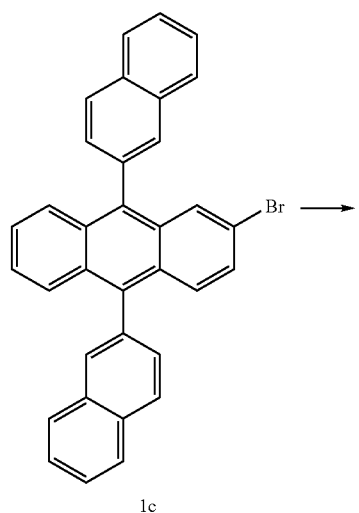
1c

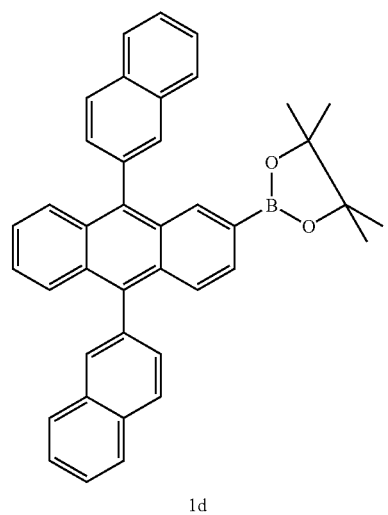
1d

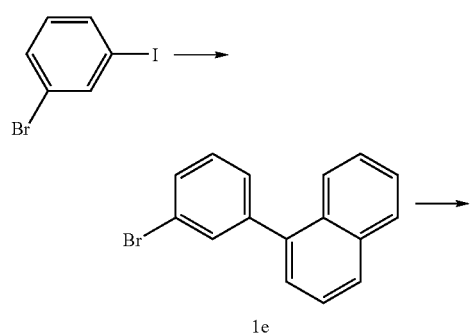
1e

-continued

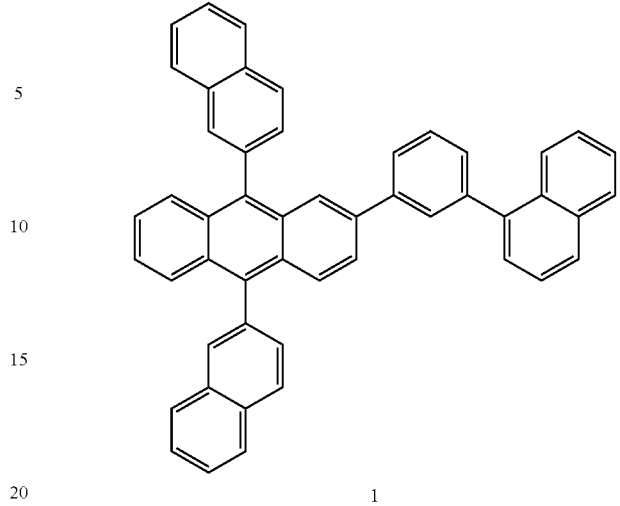
1

1-A. Production of Compound 1a

After copper bromide (18 g, 80.0 mmol) and t-butyl nitride (12 mL, 101 mmol) were dispersed in acetonitrile (250 mL) at 65° C., and then agitated, 2-aminoanthraquinone (15 g, 67.2 mmol) was slowly added thereto drop by drop for 5 min. After completion of generation of gas, the reaction solution was cooled to normal temperature and then added to 20% hydrochloric acid aqueous solution (1 L), and extraction was performed with dichloromethane. After the water residue was removed from the organic layer by using anhydrous magnesium sulfate, the resulting organic layer was dried at reduced pressure. Separation was performed by using column chromatography to obtain a light yellow compound 1a (14.5 g, 75%).

MS [M]=287

1-B. Production of Compound 1b 2-bromonaphthalene (111.0 g, 53.1 mmol) was dissolved in THF (100 mL) that was dried in a nitrogen atmosphere, t-butyl lithium (46.8 mL, a 1.7M pentane solution) was slowly added thereto at −78° C., agitation was performed at the same temperature for 1 hour, and the compound 1a (6.36 g, 22.0 mmol) was added. After the cooling vessel was removed, agitation was performed at normal temperature for 3 hours. After an ammonium chloride aqueous solution was added to the reaction mixture, extraction was performed by using methylene chloride. The organic layer was dried-by using anhydrous magnesium sulfate and the solvent was removed. After the obtained mixture was dissolved in a small amount of ethyl ether, petroleum ether was added and agitation was performed for several hours to obtain a solid compound. The solid compound was filtered and then subjected to vacuum drying to obtain a compound 1b (11.2 g, 93%).

MS [M]=543

1-C. Production of Compound 1c

After the compound 1b (11.2 g, 20.5 mmol) was dispersed in an acetic acid (200 mL) in a nitrogen atmosphere, potassium iodide (34 g, 210 mmol) and sodium hypophosphite hydrate (37 g, 420 mmol) were added thereto and then boiled for 3 hours while agitation was performed. After cooling was performed at normal temperature, the resulting substance was filtered, washed with water and methanol, and subjected to vacuum drying to obtain a light yellow compound 1c (7.2 g, 64%).

MS [M]=509

1-D. Production of Compound 1d

The compound 1c (5 g, 9.81 mmol), bis(pinacolrato)diboron (2.75 g, 10.9 mmol), potassium acetate (2.89 g, 29.4 mmol), and palladium(diphenyl phosphinoferrocene) chloride (0.24 g, 3 mol %) were put into a 250 mL flask in a nitrogen atmosphere, dioxane (50 mL) was added thereto, and the resulting mixture was refluxed at 80° C. for 6 hours. After the reaction solution was cooled to normal temperature, distilled water (50 mL) was added and extraction was performed by using methylene chloride (50 mL 3). Methylene chloride was removed at reduced pressure to obtain a light yellow solid. The light yellow solid was washed with ethanol and dried to obtain a compound 1d (5.46 g, 92%).

MS [M]=556

1-E. Production of Compound 1e

After 1-bromo-3-iodobenzene (10 g, 35.35 mmol) and 1-naphthalene bromic acid (5.47 g 31.82 mmol) were dissolved in anhydrous THF (100 mL), Pd(PPh$_3$)$_4$ (1.2 g, 1.06 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 1e (7.0 g, 70%).

MS [M+H]=283

1-F. Production of Compound 1

After the compound 1e (3.8 g, 13.42 mmol) and the compound 1d (8.96 g, 16.1 mmol) were dissolved in anhydrous THF (100 mL), Pd(PPh$_3$)$_4$ (0.47 g, 0.4 mmol) and 40 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 1 (6.5 g, 76%) represented by Formula 1-1. MS data in respects to the compound 1 are shown in FIG. 2.

MS [M+H]=632

SYNTHETIC EXAMPLE 2

Production of Compound of Formula 1-2

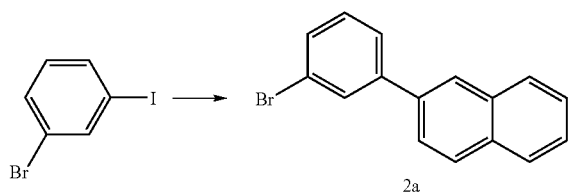

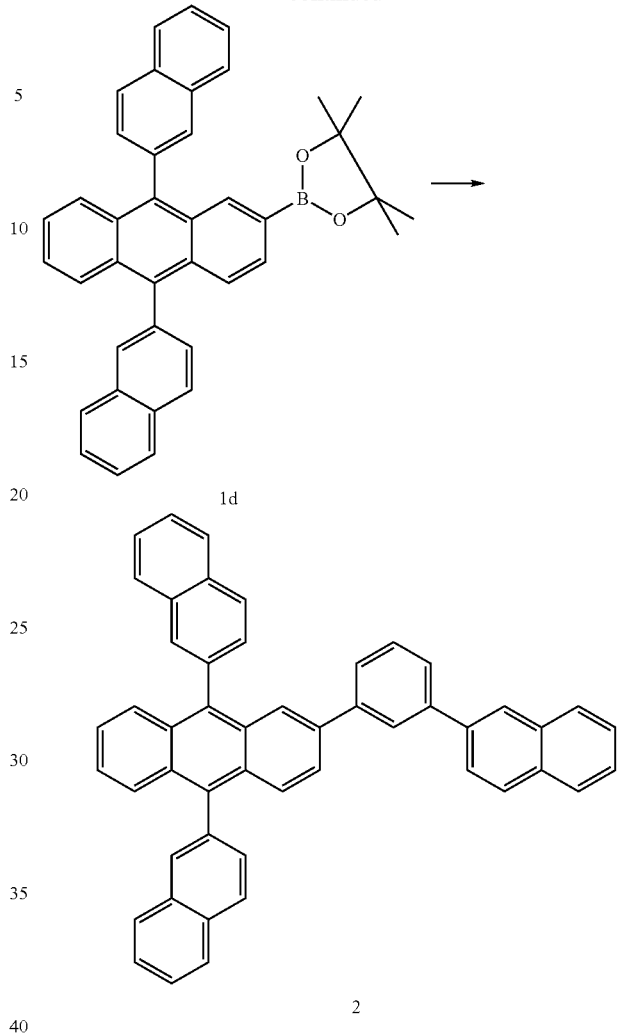

2-A. Production of Compound 2a

After 1-bromo-3-iodobenzene (10 g, 35.35 mmol) and 2-naphthalene bromic acid (5.47 g, 31.82 mmol) were dissolved in anhydrous THF (100 mL), Pd(PPh$_3$)$_4$ (1.2 g, 1.06 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 2a (8.5 g, 85%).

MS [M+H]=283

2-B. Production of Compound 2

After the compound 2a (4.0 g, 14.13 mmol) and the compound 1d (9.43 g, 16.95 mmol) were dissolved in anhydrous THF (200 mL), Pd(PPh$_3$)$_4$ (0.49 g, 0.42 mmol) and 60 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 2 (6.0 g, 67%) represented by Formula 1-2. MS data in respects to the compound 2 are shown in FIG. 3.

MS [M+H]=632

SYNTHETIC EXAMPLE 3

Production of Compound of Formula 1-3

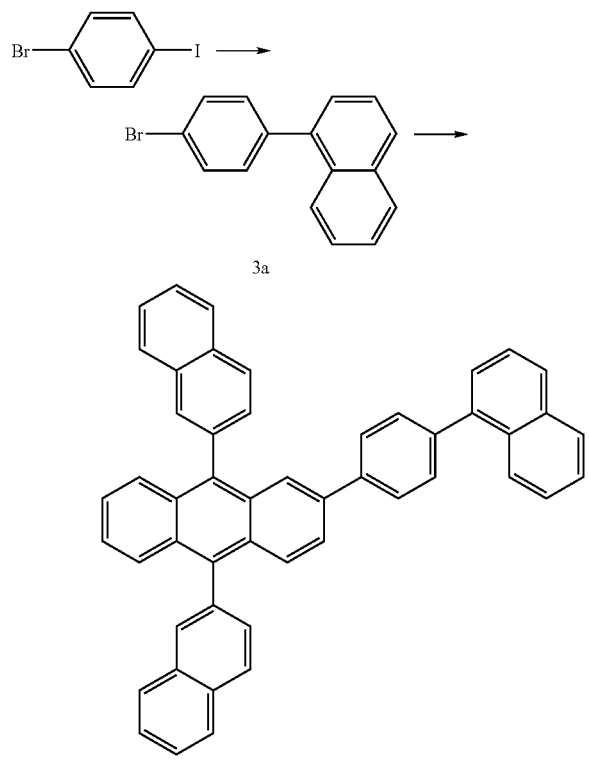

3

MS [M+H]=632

SYNTHETIC EXAMPLE 4

Production of Compound of Formula 1-4

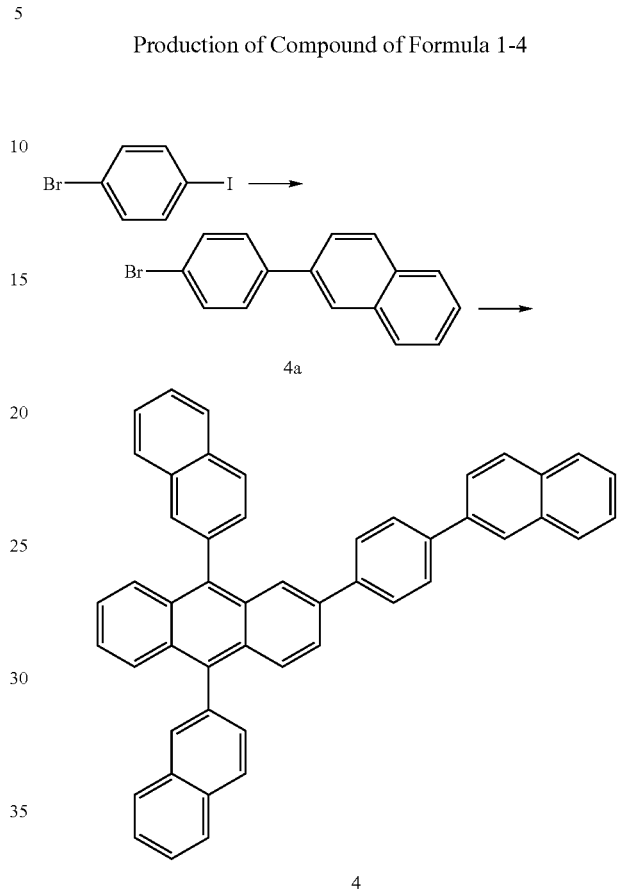

4

3-A. Production of Compound 3a

After 1-bromo-4-iodobenzene (10 g, 35.35 mmol) and 1-naphthalene bromic acid (5.47 g, 31.82 mmol) were dissolved in anhydrous THF (100 mL), Pd(PPh$_3$)$_4$ (1.2 g, 1.06 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 3a (8.0 g, 80%).

MS [M+H]=283

3-B. Production of Compound 3

After the compound 3a (4.0 g, 14.13 mmol) and the compound 1d (9.43 g, 16.95 mmol) were dissolved in anhydrous THF (200 mL), Pd(PPh$_3$)$_4$ (0.49 g, 0.42 mmol) and 60 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 3 (7.5 g, 84%) represented by Formula 1-3.

4-A. Production of Compound 4a

After 1-bromo-4-iodobenzene (10 g, 35.35 mmol) and 2-naphthalene bromic acid (5.47 g, 31.82 mmol) were dissolved in anhydrous THF (100 mL), Pd(PPh$_3$)$_4$ (1.2 g, 1.06 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 4a (7.5 g, 75%).

MS [M+H]=283

4-B. Production of Compound 4

After the compound 4a (4.0 g, 14.13 mmol) and the compound 1d (9.43 g, 16.95 mmol) were dissolved in anhydrous THF (200 mL), Pd(PPh$_3$)$_4$ (0.49 g, 0.42 mmol) and 60 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 4 (6.8 g, 76%) represented by Formula 1-4.

MS [M+H]=632

SYNTHETIC EXAMPLE 5

Production of Compound of Formula 1-5

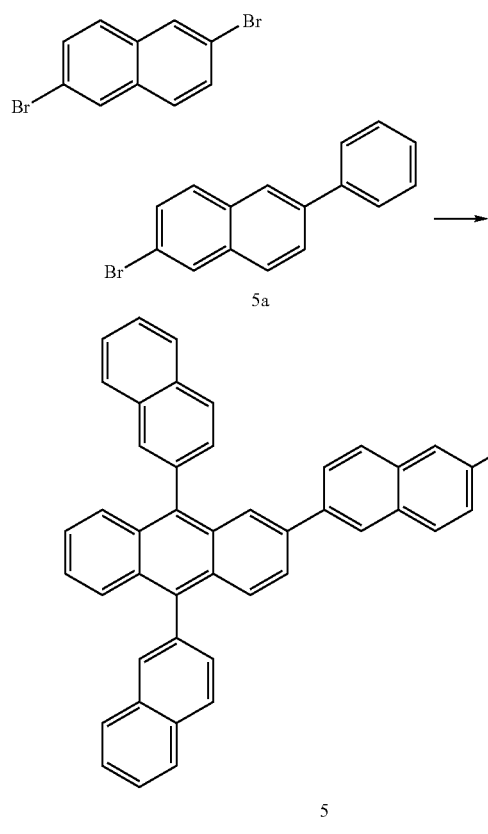

5

MS [M+H]=632

SYNTHETIC EXAMPLE 6

Production of Compound of Formula 1-6

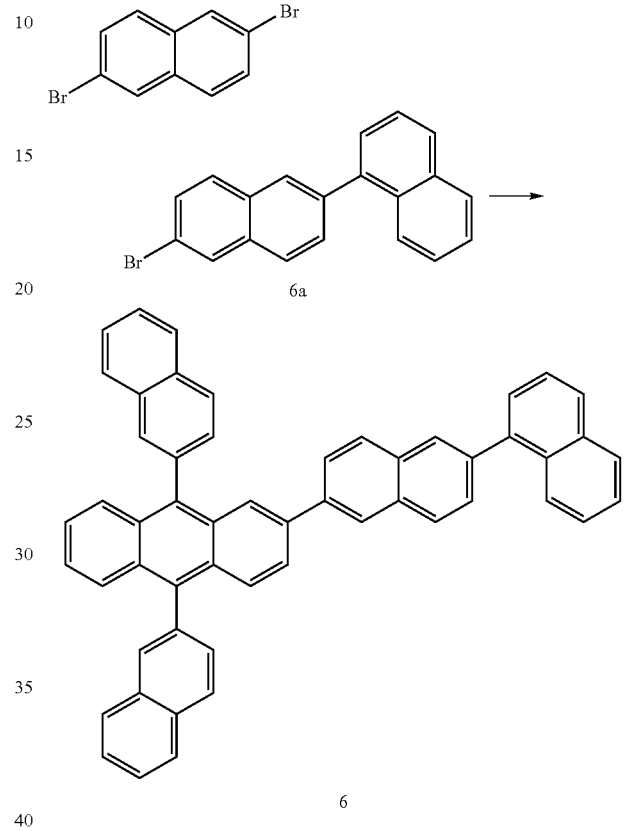

6

5-A. Production of Compound 5a

After 2,6-dibromonaphthalene (5 g, 17.48 mmol) and phenyl bromic acid (1.06 g, 8.74 mmol) were dissolved in anhydrous THF (100 mL), Pd(PPh$_3$)$_4$ (0.3 g, 0.26 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 5a (1.8 g, 73%).

MS [M+H]=283

5-B. Production of Compound 5

After the compound 5a (1.8 g, 6.36 mmol) and the compound 1d (4.25 g, 7.63 mmol) were dissolved in anhydrous THF (50 mL), Pd(PPh$_3$)$_4$ (0.22 g, 0.19 mmol) and 20 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 5 (3.7 g, 92%) represented by Formula 1-5. MS data in respects to the compound 5 are shown in FIG. 4.

6-A. Production of Compound 6a

After 2,6-dibromonaphthalene (5 g, 17.48 mmol) and 1-naphthalene bromic acid (1.5 g, 8.74 mmol) were dissolved in anhydrous THF (100 mL), Pd(PPh$_3$)$_4$ (0.3 g, 0.26 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 6a (2.1 g, 72%).

MS [M+H]=283

6-B. Production of Compound 6

After the compound 6a (2.1 g, 6.36 mmol) and the compound 1d (4.25 g, 7.63 mmol) were dissolved in anhydrous THF (550 mL), Pd(PPh$_3$)$_4$ (0.22 g, 0.19 mmol) and 20 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 6 (3.9 g, 90%) represented by Formula 1-6.

MS [M+H]=682

SYNTHETIC EXAMPLE 7

Production of Compound of Formula 1-7

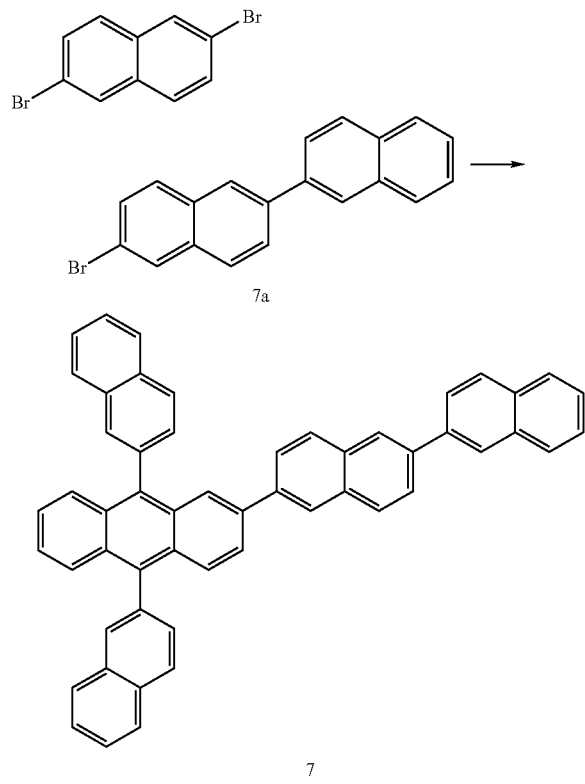

7-A. Production of Compound 7a

After 2,6-dibromonaphthalene (5 g, 17.48 mmol) and 2-naphthalene bromic acid (1.5 g, 8.74 mmol) were dissolved in anhydrous THF (100 mL), Pd(PPh$_3$)$_4$ (0.3 g, 0.26 mmol) and 50 mL of 2M K$_2$CO$_3$ aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 7a (2.7 g, 93%).

MS [M+H]=283

7-B. Production of Compound 7

After the compound 7a (2.1 g, 6.36 mmol) and the compound 1d (4.25 g, 7.63 mmol) were dissolved in anhydrous THF (50 mL), Pd(PPh$_3$)$_4$ (0.2° g, 0.19 mmol) and 20 mL of 2M K$_2$CO$_3$, aqueous solution were added and then refluxed for 24 hours. The organic layer was extracted by using ethyl acetate and water was removed with magnesium sulfate. The organic layer was filtered at reduced pressure and concentrated, and the solvent was removed. The resulting substance was purified by using column chromatography and then recrystallized in THF and ethanol to obtain a white solid compound 7 (3.8 g, 87%) represented by Formula 1-7.

MS [M+H]=682

EXPERIMENTAL EXAMPLE 1

A glass substrate (7059 glass, Corning, Co.) on which a thin film of ITO (indium tin oxide) was formed to a thickness of 1,000 Å was immersed in distilled water containing a dispersing agent to be washed with an ultrasonic wave. The product manufactured by Fisher Co. was used as the dispersing agent, and the distilled water was filtered twice by using a filter manufactured by Millipore Co. After the ITO was washed for 30 min, the ultrasonic wave washing was repeated twice for 10 minutes by using distilled water. After completion of the washing using distilled water, the ultrasonic wave washing was carried out by using a solvent such as isopropyl alcohol, acetone, and methanol. The resulting product was dried and transported to a plasma cleaner. Then, the substrate was cleaned for 5 minutes by using an oxygen plasma and then transported to a vacuum deposition device.

On the ITO electrode, 3,6-bis-2-naphthylphenylamino-N-[4-(2-naphthylphenyl)aminophenyl]carbazole (800 Å), 4,4'-bis[N-(1-naphthyl)-N-phenylamino]biphenyl (NPB) (300 Å), and the compound 1 that was produced in Synthetic Example 1 were deposited in conjunction with the following compound N (4 wt %) (0.300 Å). Subsequently, 9,10-bis-2-naphthyl-2-[4-(N-phenylbenzoimidazoyl)phenyl]anthracene (200 Å) was deposited in a vacuum by heating to sequentially form a hole injecting layer, a hole transporting layer, a light emitting layer, and an electron transporting layer.

On the electron transporting layer, lithium fluoride (LiF) and aluminum were sequentially deposited to a thickness of 12 Å and 2,000 Å, respectively, to form a cathode. Thereby, the organic light emitting device was produced.

During the above-mentioned process, the deposition rate of the organic material was maintained at 0.6 to 1.0 Å/sec, the deposition rate of lithium fluoride of the cathode was maintained at 0.3 Å/sec, the deposition rate of aluminum was maintained at 2 Å/sec, and the degree of vacuum was maintained at $2 \times 10^{-7}$ to $5 \times 10^{-8}$ torr during the deposition.

When a forward electric field of 8.5 V was applied to the produced organic light emitting device, green light emission of 17.5 cd/A was observed at a current density of 100 mA/□. In terms of the color coordinate x was 0.313 and y was 0.639.

[Compound N]

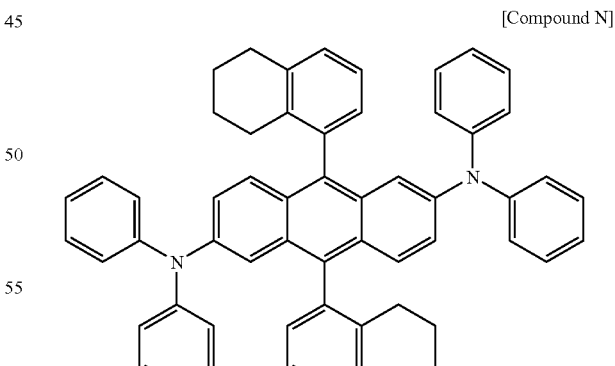

EXPERIMENTAL EXAMPLE 2

The organic light emitting device was produced by using the same procedure as Experimental Example 1, except that the compound 2 was used instead of the compound 1 of Experimental Example 1.

When a forward electric field of 8.42 V was applied to the produced organic light emitting device, green light emission of 18.8 cd/A corresponding to the 1931 CIE color coordinate in which x=0.315 and y=0.638 was observed at a current density of 100 mA/□.

EXPERIMENTAL EXAMPLE 3

The organic light emitting device was produced by using the same procedure as Experimental Example 1, except that the compound 3 was used instead of the compound 1 of Experimental Example 1.
When a forward electric field of 8.6 V was applied to the produced organic light emitting device, green light emission of 17.9 cd/A corresponding to the 1931 CIE color coordinate in which x=0.323 and y=0.649 was observed at a current density of 100 mA/□.

EXPERIMENTAL EXAMPLE 4

The organic light emitting device was produced by using the same procedure as Experimental Example 1, except that the compound 4 was used instead of the compound 1 of Experimental Example 1.
When a forward electric field of 8.5 V was applied to the produced organic light emitting device, green light emission of 18 cd/A corresponding to the 1931 CIE color coordinate in which x=0.325 and y=0.651 was observed at a current density of 100 mA/□.

EXPERIMENTAL EXAMPLE 5

The organic light emitting device was produced by using the same procedure as Experimental Example 1, except that the compound 5 was used instead of the compound 1 of Experimental Example 1.
When a forward electric field of 8.5 V was applied to the produced organic light emitting device, green light emission of 18.1 cd/A corresponding to the 1931 CIE color coordinate in which x=0.320 and y=0.636 was observed at a current density of 100 mA/□.

EXPERIMENTAL EXAMPLE 6

The organic light emitting device was produced by using the same procedure as Experimental Example 1, except that the compound 6 was used instead of the compound 1 of Experimental Example 1.
When a forward electric field of 8.6 V was applied to the produced organic light emitting device, green light emission of 18.2 cd/A corresponding to the 1931 CIE color coordinate in which x=0.330 and y=0.638 was observed at a current density of 100 mA/□.

EXPERIMENTAL EXAMPLE 7

The organic light emitting device was produced by using the same procedure as Experimental Example 1, except that the compound 7 was used instead of the compound 1 of Experimental Example 1.
When a forward electric field of 8.4 V was applied to the produced organic light emitting device, green light emission of 18.2 cd/A corresponding to the 1931 CIE color coordinate in which x=0.331 and y=0.637 was observed at a current density of 100 mA/□.

The invention claimed is:
1. An anthracene derivative represented by the Formula 1:

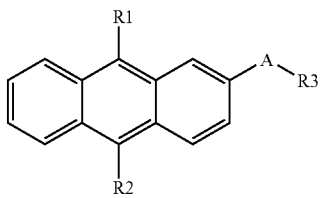

[Formula 1]

wherein R1, R2, and R3 are each independently a $C_6$ to $C_{20}$ aryl group, and

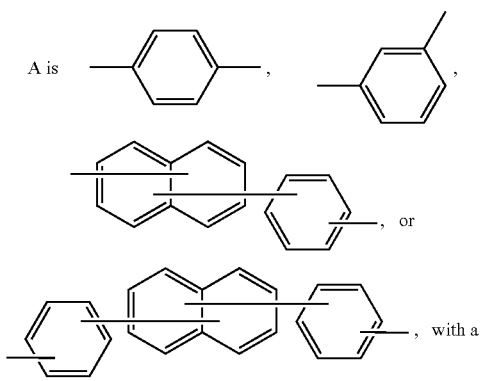

A is ———, ———, ———, or ———, with a proviso that R3 is selected from the group consisting of naphthyl, phenylnaphthyl and binaphthyl when A is

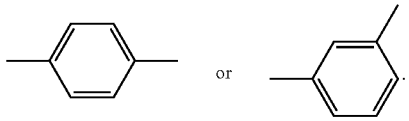

2. The anthracene derivative according to claim 1, wherein in the Formula 1, R1, R2, and R3 are each independently any one selected from the group consisting of phenyl, naphthyl, and biphenyl.

3. An organic electronic device comprising the anthracene derivative according to claim 2.

4. The anthracene derivative according to claim 1, wherein in the Formula 1, A is any one selected from the group consisting of the following substituent groups:

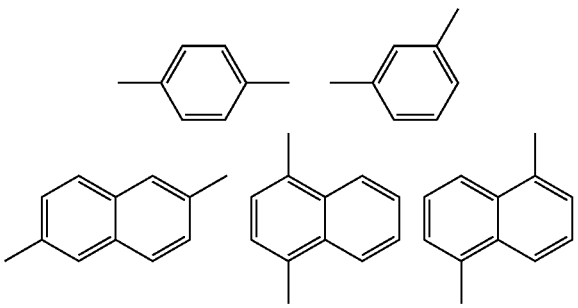

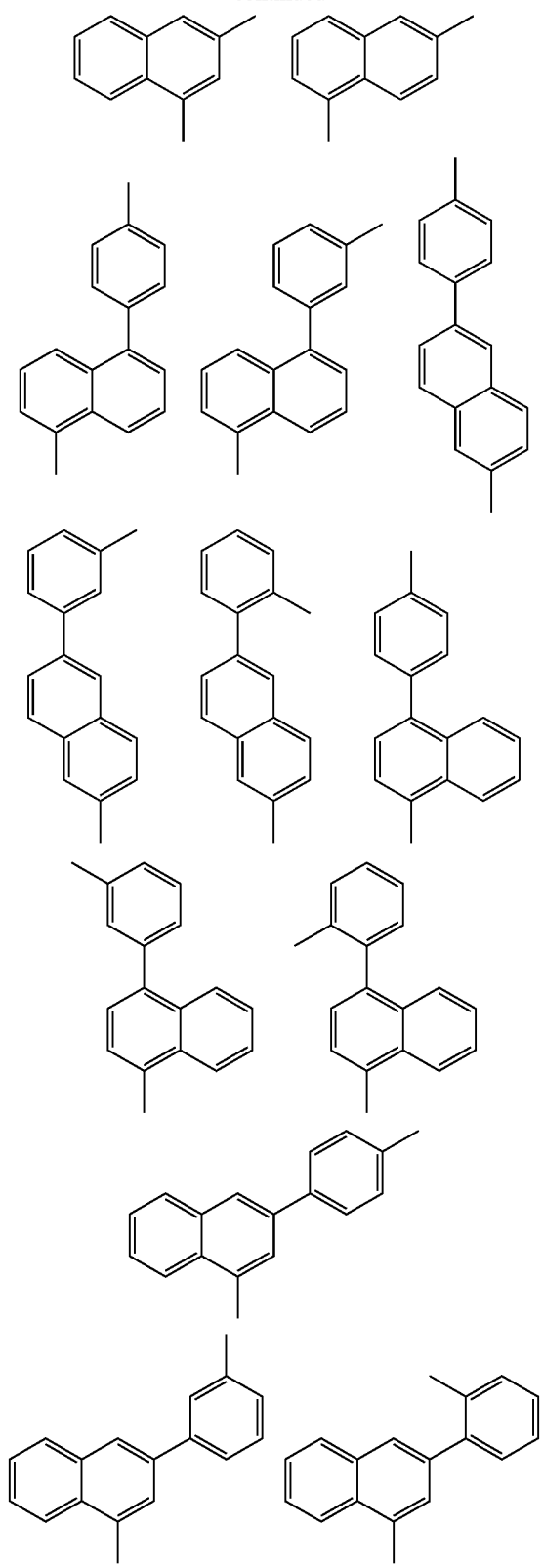
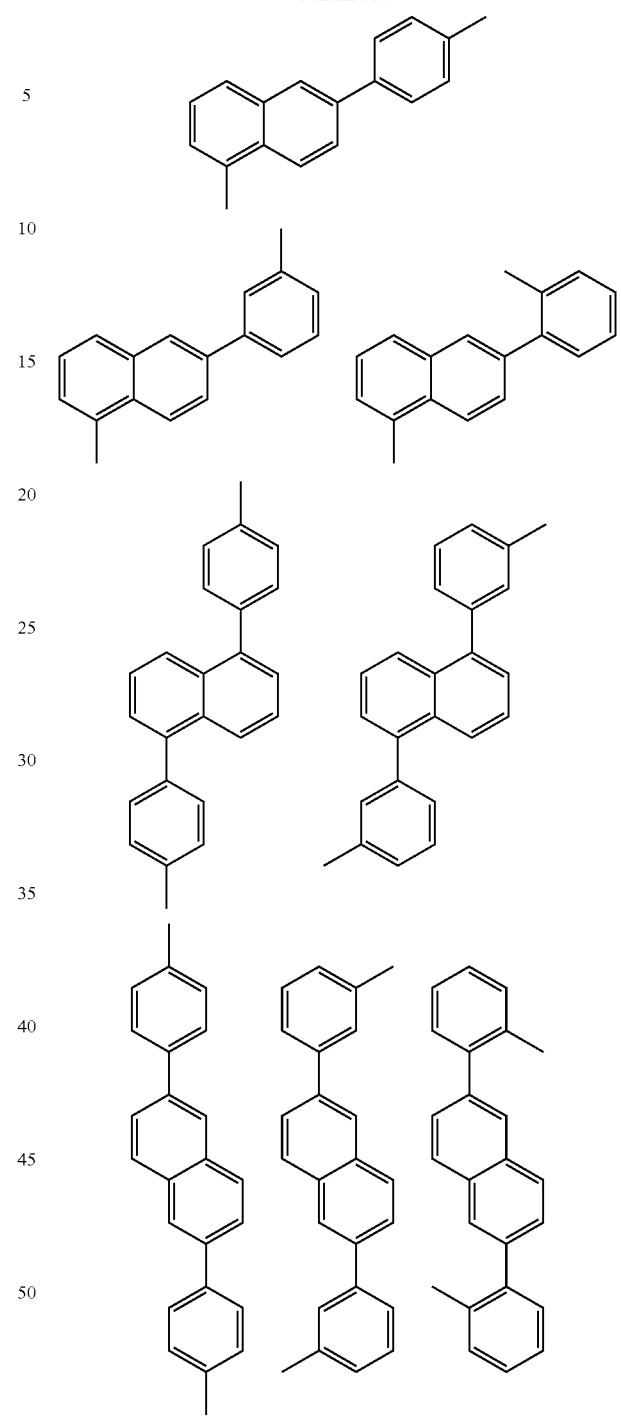

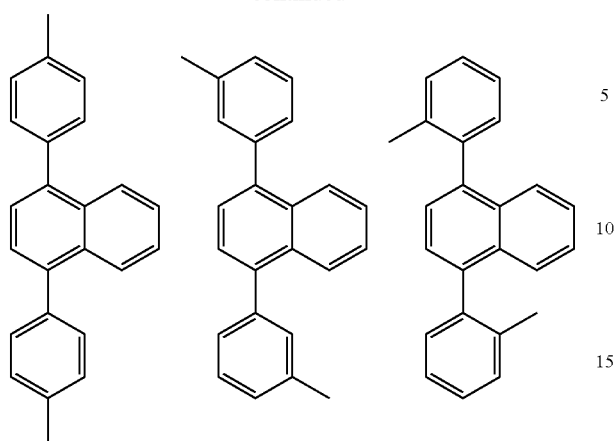
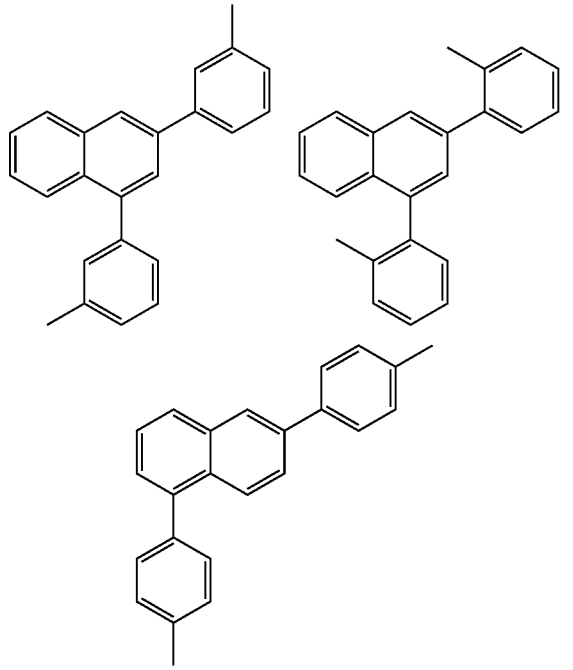
5. An organic electronic device comprising the anthracene derivative according to claim 4.
6. The anthracene derivative according to claim 1, wherein the anthracene derivative is any one of compounds represented by the Formulas 1-1 to 1-27:
<Formula 1-1>

<Formula 1-2>
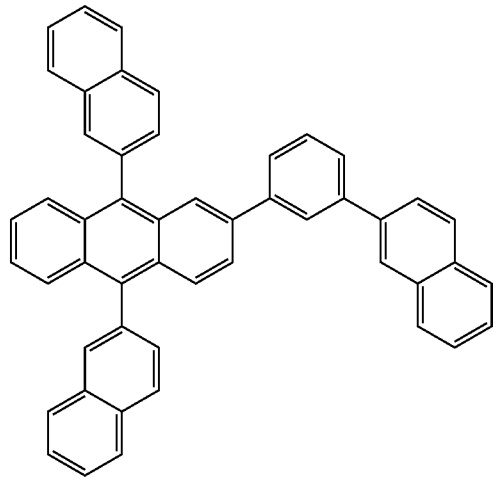
<Formula 1-3>
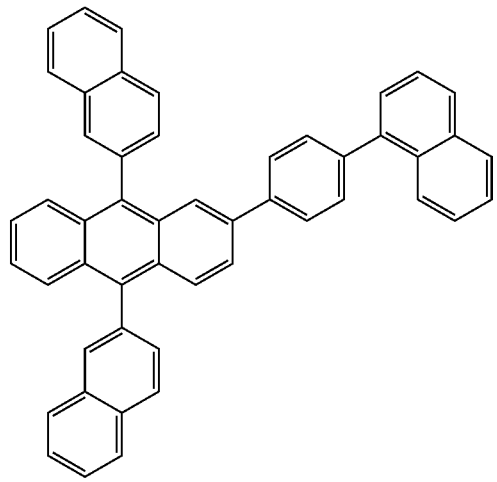
<Formula 1-4>
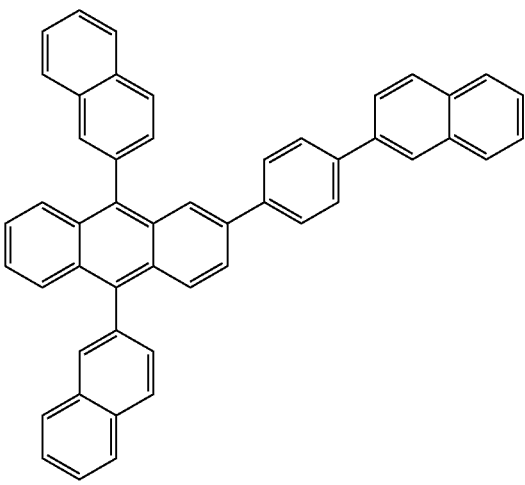
<Formula 1-5>
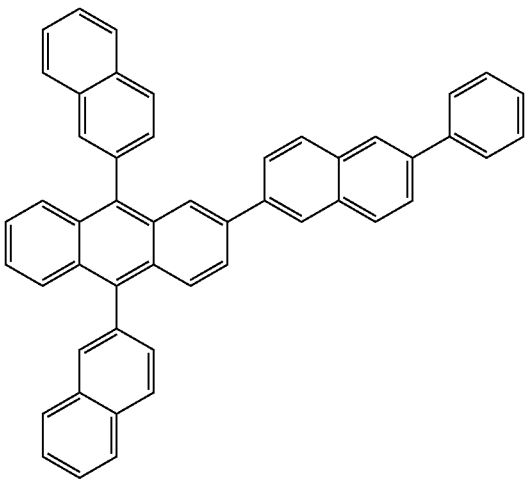
<Formula 1-6>
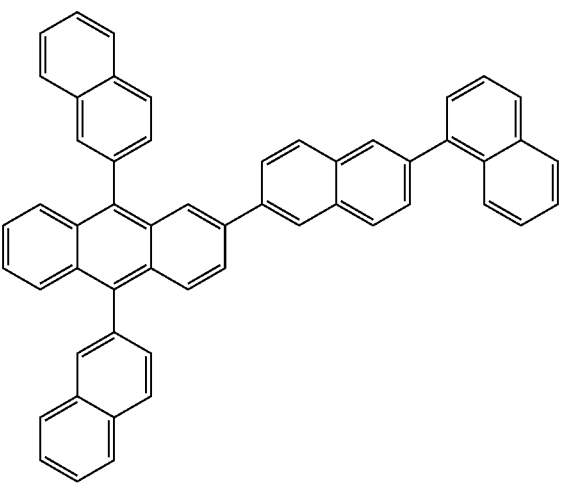
<Formula 1-7>
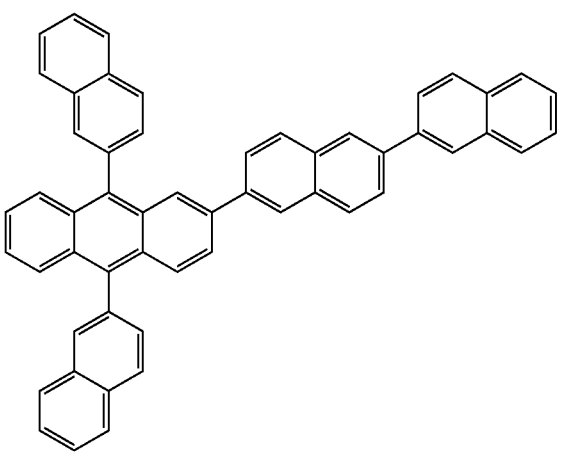

<Formula 1-8>
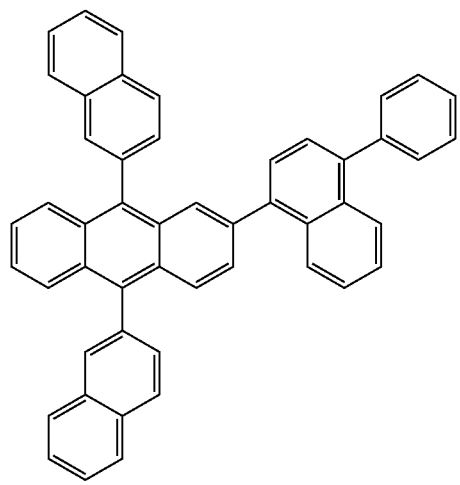
<Formula 1-9>
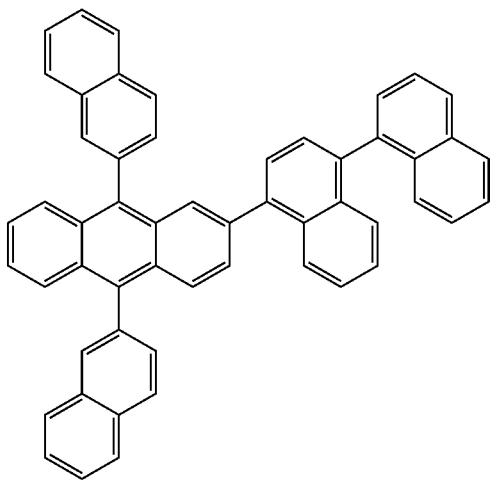
<Formula 1-10>
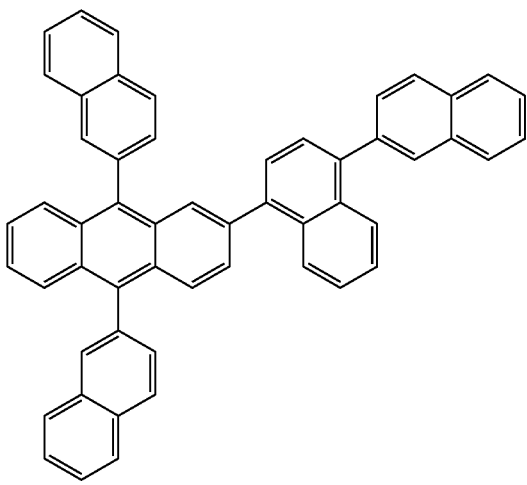
<Formula 1-11>
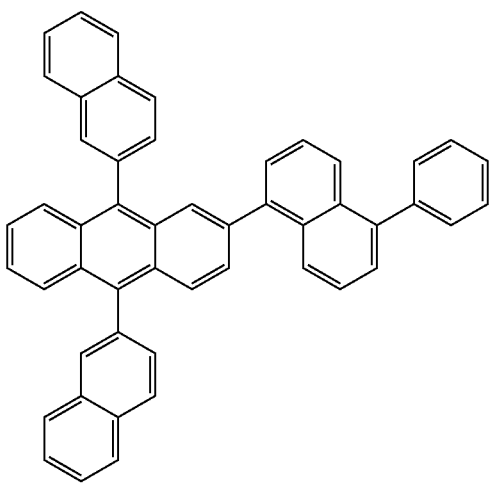
<Formula 1-12>
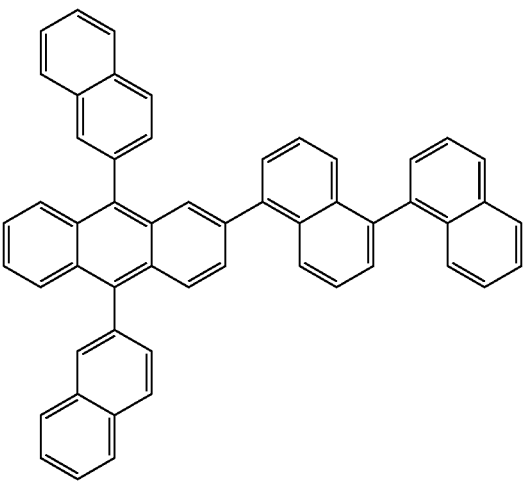
<Formula 1-13>
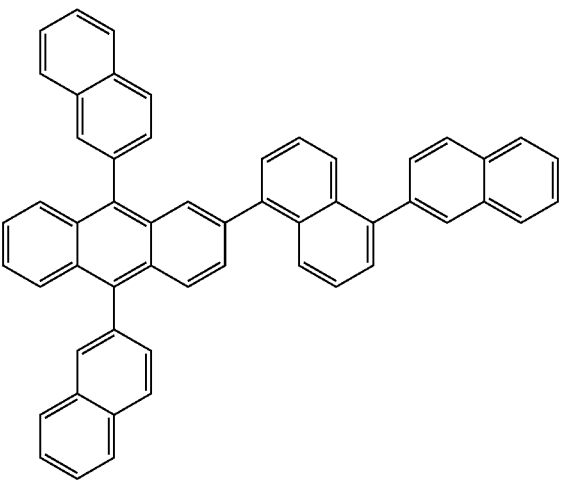

<Formula 1-14>
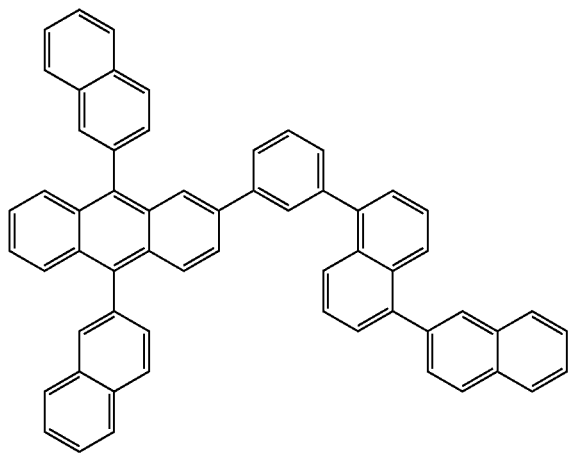
<Formula 1-15>
<Formula 1-16>
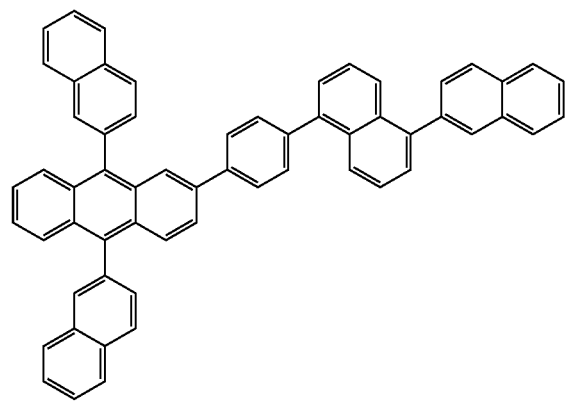
<Formula 1-17>
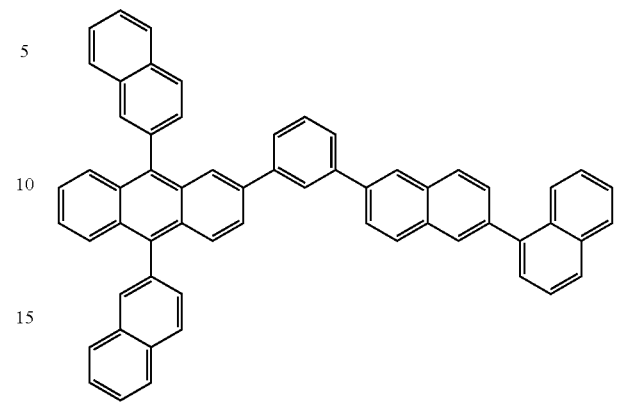
<Formula 1-18>
<Formula 1-19>
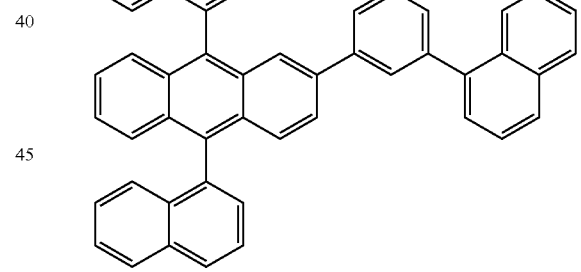
<Formula 1-20>
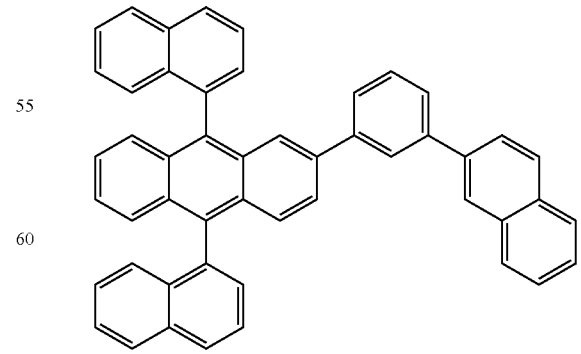

<Formula 1-21>
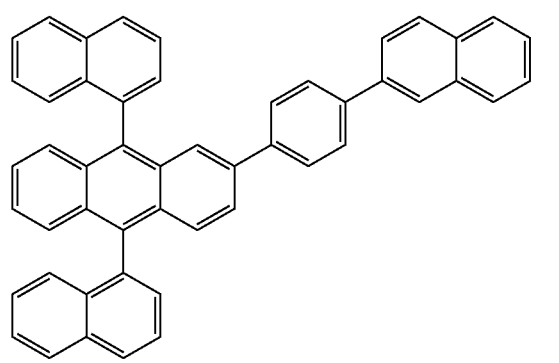

<Formula 1-25>
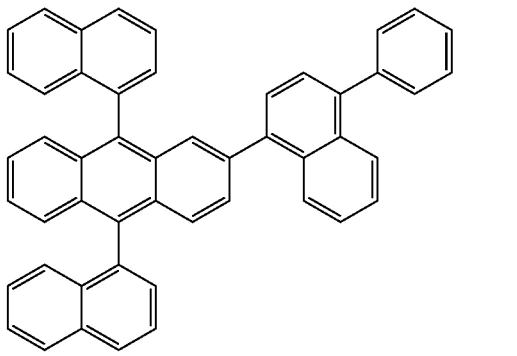

<Formula 1-22>
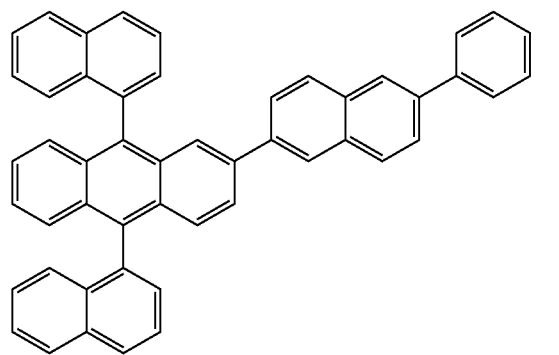

<Formula 1-26>
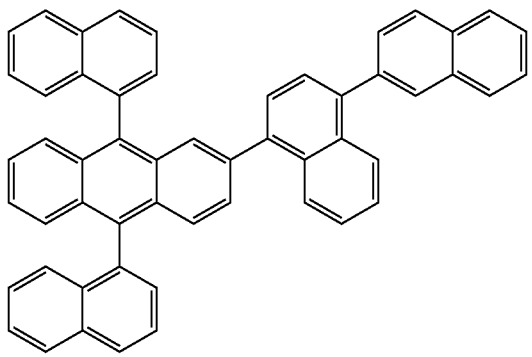

<Formula 1-23>
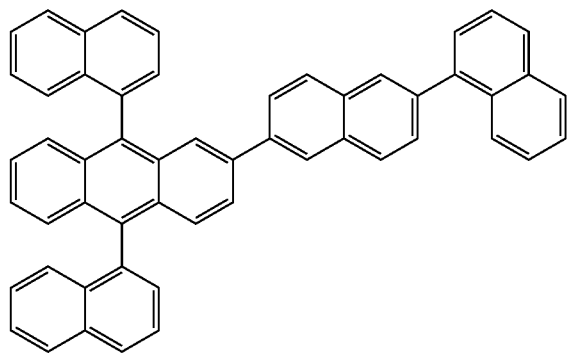

<Formula 1-27>
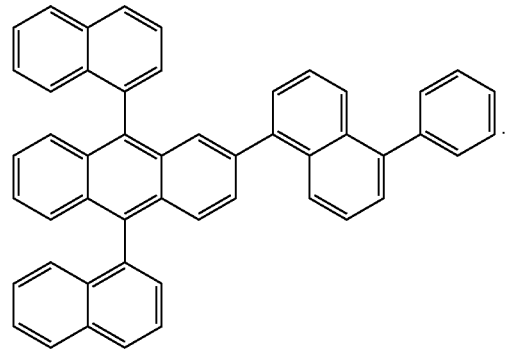

<Formula 1-24>
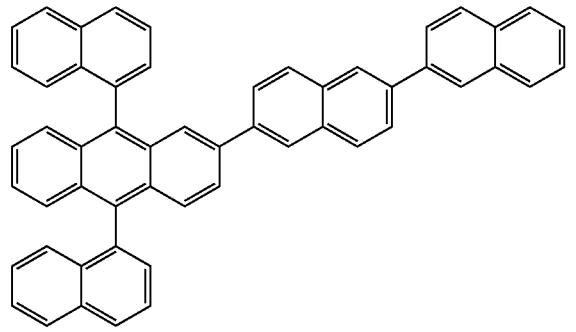

7. An organic electronic device comprising the anthracene derivative according to claim 6.

8. An organic electronic device comprising the anthracene derivative according to claim 1.

9. The organic electronic device according to claim 8, wherein the organic electronic device is any one of an organic light emitting device, an organic solar cell, an organic photoconductor (OPC), an organic transistor, an organic laser, an electromagnetic wave blocking film, a capacitor, and a memory device.

10. The organic electronic device according to claim 8, wherein the organic electronic device comprises a first electrode, a second electrode, and at least one organic material layers that are interposed between the first electrode and the second electrode, and at least one of the organic material layers comprises the anthracene derivative.

11. The organic electronic device according to claim 10, wherein the organic electronic device is an organic light emitting device that comprises organic material layers having at least one layer of a hole injecting layer, a hole transporting layer, a light emitting layer, an electron injecting layer, and an electron transporting layer, and any one layer of the organic material layers comprises the anthracene derivative.

12. An electronic apparatus comprising the organic electronic device according to claim 8.

13. The electronic apparatus according to claim 12, wherein the electronic apparatus is selected from the group consisting of a display apparatus, a smart card, a sensor, and an electronic tag (RFID; Radio Frequency Identification).

14. A method of producing an anthracene derivative according to claim 1, comprising:
 reacting a halide aryl compound and an anthracene boron compound which is substituted with aryl groups at 9 and 10 positions in the presence of a palladium catalyst.

* * * * *